(12) United States Patent
Lamberth et al.

(10) Patent No.: US 10,111,433 B2
(45) Date of Patent: Oct. 30, 2018

(54) FUNGICIDAL COMPOSITIONS

(71) Applicant: Syngenta Participations AG, Basel (CH)

(72) Inventors: Clemens Lamberth, Stein (CH); Sarah Sulzer-Mosse, Stein (CH); Laura Quaranta, Stein (CH); Michael Oostendorp, Stein (CH); Mathias Blum, Stein (CH); David Beattie, Basel (CH); Filippo De Simone, Munchwilen (CH)

(73) Assignee: SYNGENTA PARTICIPATIONS AG, Basel (CH)

( * ) Notice: Subject to any disclaimer, the term of this patent is extended or adjusted under 35 U.S.C. 154(b) by 0 days.

(21) Appl. No.: 15/328,972

(22) PCT Filed: Jul. 13, 2015

(86) PCT No.: PCT/EP2015/065922
§ 371 (c)(1),
(2) Date: Jan. 25, 2017

(87) PCT Pub. No.: WO2016/015979
PCT Pub. Date: Feb. 4, 2016

(65) Prior Publication Data
US 2017/0208808 A1 Jul. 27, 2017

(30) Foreign Application Priority Data
Jul. 31, 2014 (EP) .................................... 14179389

(51) Int. Cl.
| | | |
|---|---|---|
| A01N 43/56 | (2006.01) | |
| A01N 37/18 | (2006.01) | |
| A01N 43/38 | (2006.01) | |
| A01N 37/34 | (2006.01) | |
| A01N 47/08 | (2006.01) | |
| A01N 43/32 | (2006.01) | |
| A01N 43/54 | (2006.01) | |
| A01N 43/84 | (2006.01) | |
| A01N 43/40 | (2006.01) | |
| A01N 47/28 | (2006.01) | |
| A01N 43/653 | (2006.01) | |
| A01N 43/90 | (2006.01) | |
| A01N 43/50 | (2006.01) | |
| A01N 43/76 | (2006.01) | |
| A01N 57/12 | (2006.01) | |

(52) U.S. Cl.
CPC ............. *A01N 43/56* (2013.01); *A01N 37/18* (2013.01); *A01N 37/34* (2013.01); *A01N 43/32* (2013.01); *A01N 43/38* (2013.01); *A01N 43/40* (2013.01); *A01N 43/50* (2013.01); *A01N 43/54* (2013.01); *A01N 43/653* (2013.01); *A01N 43/76* (2013.01); *A01N 43/84* (2013.01); *A01N 43/90* (2013.01); *A01N 47/08* (2013.01); *A01N 47/28* (2013.01); *A01N 57/12* (2013.01)

(58) Field of Classification Search
CPC ......... A01N 43/56; A01N 37/18; A01N 43/32
USPC ................................. 514/75; 504/130, 139
See application file for complete search history.

(56) References Cited

U.S. PATENT DOCUMENTS 8,367,844 B2 * 2/2013 Sulzer-Mosse ...... C07D 231/12
504/239

FOREIGN PATENT DOCUMENTS

| | | |
|---|---|---|
| EP | 12729648.1 | 8/2014 |
| WO | 2011018415 A2 | 2/2011 |
| WO | 2013000943 A1 | 1/2013 |
| WO | WO 2013000943 A1 * | 1/2013 ........... C07D 401/06 |

OTHER PUBLICATIONS

ISR and Written Opinion of PCT/EP2015/065922.
Olivier Sauvageot, "EP12729648.1, Applicant Reply Apr. 8, 2014" European Patent Register, Aug. 4, 2014 (Aug. 4, 2014), XP055210302.

* cited by examiner

*Primary Examiner* — Craig D Ricci
*Assistant Examiner* — Janet L. Coppins

(57) ABSTRACT

A composition suitable for control of diseases caused by phytopathogens comprising (A) a compound of formula (I) wherein $R^1$ is difluoromethyl or trifluoromethyl and $R^2$ is methyl, difluoromethyl, trifluoromethyl or cyclopropyl; and (B) at least one compound selected from compounds known for their fungicidal activity; and a method of controlling diseases on useful plants, especially leaf spot diseases on cereals.

(I)

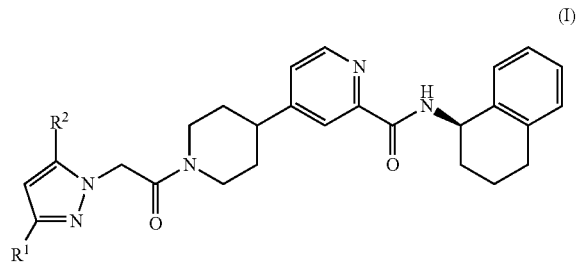

4 Claims, No Drawings

FUNGICIDAL COMPOSITIONS

RELATED APPLICATION INFORMATION

This application is a 371 of International Application No. PCT/EP2015/065922, filed Jul. 13, 2015, which claims priority to EP14179389.3, filed Jul. 31, 2014, the contents of which are incorporated herein by reference herein.

The present invention relates to novel fungicidal compositions suitable for control of diseases caused by phytopathogens, especially phytopathogenic fungi and to a method of controlling diseases on useful plants, especially fruits and vegetables.

It is known from WO 2011/018415 and WO 2013/000943 that certain pyrazole derivatives and mixtures comprising said pyrazole derivatives have biological activity against phytopathogenic fungi. On the other hand various fungicidal compounds of different chemical classes are widely known as plant fungicides for application in various crops of cultivated plants. However, crop tolerance and activity against phytopathogenic plant fungi do not always satisfy the needs of agricultural practice in many incidents and aspects. For example, *Phytophthora infestans*, the late blight disease of potato and tomato, and *Plasmopara viticola*, the downy mildew disease of grape become an increasingly important problem in fruit and vegetable production, resulting in considerable yield losses. Many customary fungicides are unsuitable for controlling late blight of potato and tomato and downy mildew of grape or their action against *Phytophthora infestans* and *Plasmopara viticola* is unsatisfactory.

Out of the above-mentioned needs of agricultural practice for increased crop tolerance and/or increased activity against phytopathogenic fungi, such as *Phytophthora infestans* and *Plasmopara viticola*, there is therefore proposed in accordance with the present invention a novel composition suitable for control of diseases caused by phytopathogens comprising: (A) a compound of formula I

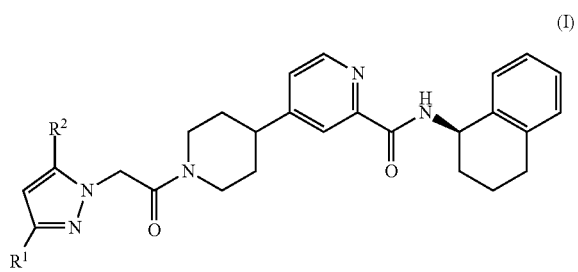

(I)

wherein $R^1$ is difluoromethyl or trifluoromethyl and $R^2$ is methyl, difluoromethyl, trifluoromethyl or cyclopropyl; and (B) at least one compound selected from the group consisting of
(B1) a strobilurin fungicide,
(B2) an azole fungicide,
(B3) a morpholine fungicide,
(B4) an anilinopyrimidine fungicide,
(B5) a carboxamide fungicide,
(B6) a phenylamide fungicide,
(B7) a carboxlic acid amide fungicide,
(B8) a fungicide selected from the group consisting of etridiazole, fluazinam, benalaxyl-M, dodicin, N'-(2,5-Dimethyl-4-phenoxy-phenyl)-N-ethyl-N-methyl-formamidine, N'-[4-(4,5-Dichloro-thiazol-2-yloxy)-2,5-dimethyl-phenyl]-N-ethyl-N-methyl-formamidine, N'-[4-[[3-[(4-chlorophenyl)methyl]-1,2,4-thiadiazol-5-yl]oxy]-2,5-dimethyl-phenyl]-N-ethyl-N-methyl-formamidine, ethirimol, 3'-chloro-2-methoxy-N-[(3RS)-tetrahydro-2-oxofuran-3-yl]acet-2',6'-xylidide, dithianon, aureofungin, blasticidin-S, biphenyl, chloroneb, dicloran, hexachlorobenzene, quintozene, tecnazene, tolclofos-methyl, metrafenone, 2,6-dichloro-N-(4-trifluoromethylbenzyl)-benzamide, fluopicolide, tioxymid, flusulfamide, benomyl, carbendazim, carbendazim chlorhydrate, chlorfenazole, fuberidazole, thiabendazole, thiophanate-methyl, chlobenthiazone, probenazole, acibenzolar, bethoxazin, pyriofenone, pyribencarb, butylamine, 3-iodo-2-propinyl n-butylcarbamate, iodocarb, isopropanyl butylcarbamate, picarbutrazox, polycarbamate, propamocarb, tolprocarb, 3-(difluoromethyl)-N-(7-fluoro-1,1,3,3-tetramethyl-indan-4-yl)-1-methyl-pyrazole-4-carboxamide, diclocymet, N-[(5-chloro-2-isopropyl-phenyl)methyl]-N-cyclopropyl-3-(difluoromethyl)-5-fluoro-1-methyl-pyrazole-4-carboxamide, N-cyclopropyl-3-(difluoromethyl)-5-fluoro-N-[(2-isopropylphenyl)methyl]-1-methyl-pyrazole-4-carboxamide, carpropamid, chlorothalonil, oxine-copper, cymoxanil, phenamacril, cyazofamid, flutianil, thicyofen, chlozolinate, iprodione, procymidone, vinclozolin, bupirimate, dinocton, dinopenton, dinobuton, dinocap, meptyldinocap, diphenylamine, phosdiphen, 2,6-dimethyl-[1,4]dithiino[2,3-c:5,6-c']dipyrrole-1,3,5,7(2H,6H)-tetraone, etem, ferbam, mancozeb, maneb, metam, metiram, metiram-zinc, nabam, propineb, thiram, vapam, zineb, ziram, dithioether, isoprothiolane, ethaboxam, fosetyl, phosetyl-Al, methyl bromide, methyl iodide, methyl isothiocyanate, cyclafuramid, validamycin, streptomycin, (2RS)-2-bromo-2-(bromomethyl)glutaronitrile, dodine, doguadine, guazatine, iminoctadine, iminoctadine triacetate, 2,4-D, 2,4-DB, kasugamycin, dimethirimol, fenhexamid, hymexazole, imazalil sulphate, fenamidone, Bordeaux mixture, calcium polysulfide, copper acetate, copper carbonate, copper hydroxide, copper naphthenate, copper oleate, copper oxychloride, copper oxyquinolate, copper silicate, copper sulphate, copper tallate, cuprous oxide, sulphur, carbaryl, phthalide, dingjunezuo, oxathiapiprolin, fluoroimide, KSF-1002, benzamorf, diethofencarb, fentin acetate, fentin hydroxide, drazoxolon, famoxadone, m-phenylphenol, p-phenylphenol, tribromophenol, 2-[2-[(7,8-difluoro-2-methyl-3-quinolyl) oxy]-6-fluoro-phenyl]propan-2-ol, 2-[2-fluoro-6-[(8-fluoro-2-methyl-3-quinolyl)oxy]phenyl]propan-2-ol, cyflufenamid, flutolanil, mepronil, isofetamid, fenpiclonil, fludioxonil, pencycuron, edifenphos, iprobenfos, pyrazophos, phosphorus acids, tecloftalam, captafol, captan, ditalimfos, CAS 517875-34-2, triforine, osthol, 1-methylcyclopropene, 4-CPA, dichlorprop, dimethipin, endothal, flumetralin, forchlorfenuron, gibberellic acid, gibberellins, hymexazol, maleic hydrazide, naphthalene acetamide, paclobutrazol, prohexadione, prohexadione-calcium, thidiazuron, tribufos, trinexapac, uniconazole, α-naphthalene acetic acid, polyoxin D, BLAD, chitosan, fenoxanil, folpet, 3-(difluoromethyl)-N-methoxy-1-methyl-N-[1-methyl-2-(2,4,6-trichlorophenyl)ethyl]pyrazole-4-carboxamide, benzovindiflupyr, fenpyrazamine, diclomezine, pyrifenox, diflumetorim, fenarimol, 5-fluoro-2-(p-tolylmethoxy)pyrimidin-4-amine, ferimzone, dimetachlone, pyroquilon, proquinazid, ethoxyquin, quinoxyfen, 4,4,5-trifluoro-3,3-dimethyl-1-(3-quinolyl)isoquinoline, 4,4-difluoro-3,3-dimethyl-1-(3-quinolyl)isoquinoline, 5-fluoro-3,3,4,4-tetramethyl-1-(3-quinolyl)isoquinoline, 9-fluoro-2,2-dimethyl-5-(3-quinolyl)-3H-1,4-benzoxazepine, tebufloquin, oxolinic acid, chinomethionate, (E)-N-methyl-2-[2-(2,5-dimethylphenoxymethyl) phenyl]-2-methoxy-iminoacetamide, enestroburin, fenamistrobin, amisulbrom, dichlofluanid, tolylfluanid, but-3-ynyl N-[6-[[(Z)-[(1-methyltetrazol-5-yl)-phenyl-methylene]amino]oxymethyl]-2-pyridyl]carbamate, dazomet, benthiazole, silthiofam, zoxamide, anilazine, tricyclazole, (.+-.)-cis-1-(4-chlorophenyl)-2-(1H-1,2,4-triazol-1-yl)-cycloheptanol, 1-(5-bromo-2-pyridyl)-2-(2,4-difluorophenyl)-1,1-difluoro-3-(1,2,4-triazol-1-yl)propan-2-ol, 2-(1-tert-butyl)-1-(2-chlorophenyl)-3-(1,2,4-triazol-1-yl)-propan-2-ol, bitertanol, climbazole, dimetconazole, triazoxide, 2-[[(1R,5S)-5-[(4-fluorophenyl)methyl]-1-hydroxy-2,2-dimethyl-cyclopentyl]methyl]-4H-1,2,4-triazole-3-thione, 2-[[3-(2-chlorophenyl)-2-(2,4-difluorophenyl)oxiran-2-yl]methyl]-4H-1,2,4-triazole-3-thione, flupicolide, and ametoctradin;

(B9) a plant-bioregulator selected from the group consisting of acibenzolar-S-methyl, chlormequat chloride, ethephon, isotianil, mepiquat chloride, tiadinil and trinexapac-ethyl;

(B10) an insecticide selected from the group consisting of abamectin, acequinocyl, acetamiprid, acrinathrin, alanycarb, allethrin, alpha-cypermethrin, alphamethrin, amidoflumet, azadirachtin, azocyclotin, *bacillus firmus, bacillus thuringiensis*, bensultap, benzoximate, betacyfluthrin, bifenazate, binapacryl, bioallethrin, bioallethrin s)-cyclopentylisomer, bioresmethrin, biphenthrin, brofluthrinate, bromophos-ethyl, buprofezine, cadusafos, carbaryl, carbosulfan, cartap, chlorantraniliprole, chlorfenapyr, chromafenozide, cloethocarb, clothianidin, cyantraniliprole, cyclaniliprole, cycloprothrin, cycloxaprid, cyenopyrafen, cyflumetofen, cyfluthrin, cyhalothrin, cypermethrin, cyphenothrin, cyromazine, deltamethrin, demeton-s-methyl, diafenthiuron, dialifos, dibrom, diflovidazine, diflubenzuron, dinactin, dinocap, dinotefuran, d-limonene, emamectin, empenthrin, esfenvalerate, ethion, ethiprole, etofenprox, etoxazole, famphur, fenazaquin, fenfluthrin, fenobucarb, fenoxycarb, fenpropathrin, fenpyroximate, fenvalerate, fipronil, flometoquin, flonicamid, floupyram, fluacrypyrim, fluazuron, flubendiamide, flucythrinate, fluensulfone, flufenerim, flufenprox, flufiprole, fluhexafon, flumethrin, flupyradifuron, fluvalinate, fosthiazate, gamma-cyhalothrin, gossyplure, guadipyr, halofenozide, halofenprox, harpin, hexythiazox, hydramethylnon, imicyafos, imidacloprid, imiprothrin, indoxacarb, iodomethane, isothioate, ivermectin, lambda-cyhalothrin, lepimectin, lufenuron, metaflumizone, metaldehyde, methomyl, methoxyfenozide, metofluthrin, milbemectin, niclosamide, nitenpyram, oxamyl, parathion-ethyl, pasteuria nishizawae, p-cymene, permethrin, phenothrin, phosphocarb, piperonylbutoxide, pirimicarb, pirimiphos-ethyl, polyhedrosis virus, prallethrin, profenofos, profenofos, propargite, propetamphos, protrifenbute, pyflubumide, pymetrozine, pyraclofos, pyrafluprole, pyrethrum, pyridaben, pyridalyl, pyrifluquinazon, pyrimidifen, pyriprole, pyriproxyfen, selamectin, silafluofen, spinetoram, spinosad, spirodiclofen, spiromesifen, spirotetramat, sulfoxaflor, tebufenozide, tebufenpyrad, tefluthrin, terpenoid blends, terpenoids, tetradiphon, tetramethrin, tetranactin, tetraniliprole, theta-cypermethrin, thiacloprid, thiamethoxam, thiodicarb, tolfenpyrad, transfluthrin, trichlorfon, triflumezopyrim, zeta-cypermethrin and α-terpinene; and (B11) glyphosate.

The presence of one or more possible asymmetric carbon atoms in a compound of formula I means that the compounds may occur in optically isomeric forms, i.e. enantiomeric or diastereomeric forms. Also atropisomers may occur as a result of restricted rotation about a single bond. The present invention includes all those possible isomeric forms and mixtures thereof for a compound of formula I. Likewise, formula I is intended to include all possible tautomers. The present invention includes all possible tautomeric forms for a compound of formula I, and also a racemic compound, i.e. a mixture of at least two enantiomers in a ration of substantially 50:50.

In each case, the compounds of formula I according to the invention are in free form, in oxidized form as a N-oxide or in salt form, e.g. an agronomically usable salt form.

N-oxides are oxidized forms of tertiary amines or oxidized forms of nitrogen containing heteroaromatic compounds. They are described for instance in the book "Heterocyclic N-oxides" by A. Albini and S. Pietra, CRC Press, Boca Raton 1991.

Preferred compositions comprising (A) a compound of formula I

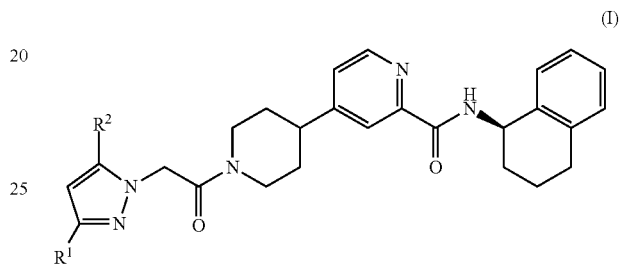

(I)

wherein $R^1$ is difluoromethyl or trifluoromethyl and $R^2$ is methyl, difluoromethyl, trifluoromethyl or cyclopropyl; and (B) at least one compound selected from the group consisting of a strobilurin fungicide selected from the group consisting of azoxystrobin, pyraclostrobin and trifloxystrobin;

an azole fungicide selected from the group consisting of cyproconazole, difenoconazole, epoxiconazole, propiconazole and prothioconazole;

an anilinopyrimidine fungicide selected from cyprodinil;

a carboxamide fungicide selected from bixafen, fluopyram, fluxapyroxad, isopyrazam, sedaxane, solatenol and 3-difluoromethyl-1-methyl-1H-pyrazole-4-carboxylic acid methoxy-[1-methyl-2-(2,4,6-trichlorophenyl)-ethyl]-amide.

a phenylamide fungicide selected from mefenoxam (metalaxyl-M) and metalaxyl;

a carboxylic acid amide fungicide selected from benthiavalicarb, dimethomorph, flumorph, iprovalicarb and mandipropamid, pyrimorph and valifenalate;

a fungicide selected from the group consisting of acibenzolar-S-methyl, ametoctradin, amisulbrom, chlorothalonil, copper, cyazofamid, cymoxanil, disodium phosphonate, dithianon, famoxadone, fenamidone, fluazinam, fludioxonil, flupicolide, folpet, fosetyl-Al, mancozeb and propamocarb.

It has been found that the use of component (B) in combination with component (A) surprisingly and substantially enhance the effectiveness of the latter against fungi, and vice versa. Additionally, the method of the invention is effective against a wider spectrum of such fungi that can be combated with the active ingredients of this method, when used solely.

A further aspect of the present invention is a method of controlling diseases on useful plants or on propagation material thereof caused by phytopathogens, which comprises applying to the useful plants, the locus thereof or propagation material thereof a composition according to the invention. Preferred is a method, which comprises applying to the useful plants or to the locus thereof a composition according to the invention, more preferably to the useful plants. Further preferred is a method, which comprises applying to the propagation material of the useful plants a composition according to the invention.

The invention covers all stereoisomers and mixtures thereof in any ratio.

A preferred embodiment of the invention is represented by those compositions which comprise as component A) a compound of formula (I), wherein $R_1$ is difluoromethyl, and most preferably wherein $R^1$ is difluoromethyl and $R^2$ is methyl, or $R^1$ is difluoromethyl and $R^2$ is difluoromethyl, or $R^1$ is difluoromethyl and $R^2$ is cyclopropyl.

These preferred compounds of formula (I) are:

1'-[2-(3-difluoromethyl-5-methyl-pyrazol-1-yl)-acetyl]-1',2',3',4',5',6'-hexahydro-[4,4']bipyridinyl-2-carboxylic acid (R)-(1,2,3,4-tetrahydronaphthalen-1-yl)-amide (compound A-1.1);

1'-[2-(3,5-bis-difluoromethyl-pyrazol-1-yl)-acetyl]-1',2',3',4',5',6'-hexahydro-[4,4']bipyridinyl-2-carboxylic acid (R)-(1,2,3,4-tetrahydronaphthalen-1-yl)-amide (compound A-1.2); and 1'-[2-(5-cyclopropyl-3-difluoromethyl-pyrazol-1-yl)-acetyl]-1',2',3',4',5',6'-hexa-hydro-[4,4']bi-pyridinyl-2-carboxylic acid (R)-(1,2,3,4-tetrahydronaphthalen-1-yl)-amide (compound A-1.3).

A further preferred embodiment of the invention is represented by those compositions which comprise as component A) a compound of formula (I), wherein $R^1$ is trifluoromethyl, and most preferably wherein $R^1$ is trifluoromethyl and $R^2$ is methyl, or $R^1$ is trifluoromethyl and $R^2$ is trifluoromethyl, or $R^1$ is trifluoromethyl and $R^2$ is cyclopropyl.

These preferred compounds of formula (I) are:

1'-[2-(5-methyl-3-trifluoromethyl-pyrazol-1-yl)-acetyl]-1',2',3',4',5',6'-hexahydro-[4,4']bipyridinyl-2-carboxylic acid (R)-(1,2,3,4-tetrahydronaphthalen-1-yl)-amide (compound A-1.4);

1'-[2-(3,5-bis-trifluoromethyl-pyrazol-1-yl)-acetyl]-1',2',3',4',5',6'-hexahydro-[4,4']bipyridinyl-2-carboxylic acid (R)-(1,2,3,4-tetrahydronaphthalen-1-yl)-amide (compound A-1.5); and 1'-[2-(5-cyclopropyl-3-trifluoromethyl-pyrazol-1-yl)-acetyl]-1',2',3',4',5',6'-hexahydro-[4,4']bi-pyridinyl-2-carboxylic acid (R)-(1,2,3,4-tetrahydro-naphthalen-1-yl)-amide (compound A-1.6).

A further preferred embodiment of the invention is represented by those compositions which comprise as component B) is a fungicide selected from acibenzolar-S-methyl, ametoctradin, amisulbrom, azoxystrobin, benthiavalicarb, bixafen, chlorothalonil, copper, cyazofamid, cymoxanil, disodium phosphonate, cyproconazole, cyprodinil, difenoconazole, dimethomorph, dithianon, epoxiconazole, famoxadone, fenamidone, fluazinam, fludioxonil, flumorph, flupicolide, fluxapyroxad, fluopyram, folpet, fosetyl-Al, iprovalicarb, isopyrazam, mancozeb, mandipropamid, mefenoxam, metalaxyl, propamocarb, propiconazole, prothioconazole, pyraclostrobin, pyrimorph, sedaxane, solatenol, trifloxystrobin, valifenalate and 3-difluoromethyl-1-methyl-1H-pyrazole-4-carboxylic acid methoxy-[1-methyl-2-(2,4,6-trichlorophenyl)-ethyl]amide.

A further preferred embodiment of the invention is represented by those compositions which comprise as component B) is a fungicide selected from a compound selected from acibenzolar-S-methyl, ametoctradin, amisulbrom, azoxystrobin, benthiavalicarb, chlorothalonil, copper, cyazofamid, cymoxanil, disodium phosphonate, dimethomorph, dithianon, famoxadone, fenamidone, fluazinam, flumorph, flupicolide, folpet, fosetyl-Al, iprovalicarb, isopyrazam, mancozeb, mandipropamid, mefenoxam, metalaxyl, pyra- clostrobin, solatenol, trifloxystrobin and 3-difluoromethyl-1-methyl-1H-pyrazole-4-carboxylic acid methoxy-[1-methyl-2-(2,4,6-trichlorophenyl)-ethyl]-amide.

Especially preferred compositions according to the invention comprise as component (A) a compound selected from 1'-[2-(3-difluoromethyl-5-methyl-pyrazol-1-yl)-acetyl]-1',2',3',4',5',6'-hexahydro-[4,4']bipyridinyl-2-carboxylic acid (R)-(1,2,3,4-tetrahydronaphthalen-1-yl)-amide (compound A-1.1), 1'-[2-(3,5-bis-difluoromethyl-pyrazol-1-yl)-acetyl]-1',2',3',4',5',6'-hexahydro-[4,4']bipyridinyl-2-carboxylic acid (R)-(1,2,3,4-tetrahydronaphthalen-1-yl)-amide (compound A-1.2) and 1'-[2-(5-cyclopropyl-3-difluoromethyl-pyrazol-1-yl)-acetyl]-1',2',3',4',5',6'-hexa-hydro-[4,4']bi-pyridinyl-2-carboxylic acid (R)-(1,2,3,4-tetrahydronaphthalen-1-yl)-amide (compound A-1.3) and as component (B) a compound selected from acibenzolar-S-methyl, ametoctradin, amisulbrom, azoxystrobin, benthiavalicarb, bixafen, chlorothalonil, copper, cyazofamid, cymoxanil, disodium phosphonate, cyproconazole, cyprodinil, difenoconazole, dimethomorph, dithianon, epoxiconazole, famoxadone, fenamidone, fluazinam, fludioxonil, flumorph, flupicolide, fluxapyroxad, fluopyram, folpet, fosetyl-Al, iprovalicarb, isopyrazam, mancozeb, mandipropamid, mefenoxam, metalaxyl, propamocarb, propiconazole, prothioconazole, pyraclostrobin, pyrimorph, sedaxane, solatenol, trifloxystrobin, valifenalate and 3-difluoromethyl-1-methyl-1H-pyrazole-4-carboxylic acid methoxy-[1-methyl-2-(2,4,6-trichlorophenyl)-ethyl]-amide.

The compounds of formula (I) may be prepared in analogous manner as outlined in WO 2011/018415 and WO 2013/000943 by chemical reactions known in the art.

Compounds of formula (I) may be obtained as described in example 1.

The invention is illustrated by the following non-limiting example.

EXAMPLE 1

This example illustrates the preparation of 1'-[2-(3,5-bis-difluoromethyl-pyrazol-1-yl)-acetyl]-1',2',3',4',5',6'-hexahydro-[4,4']bipyridinyl-2-carboxylic acid (R)-(1,2,3,4-tetrahydronaphthalen-1-yl)-amide (compound A-1.2)

a) Preparation of 3,6-dihydro-2H-[4,4']bipyridinyl-1,2'-dicarboxylic acid 1-tert-butyl ester To a solution of 4-bromopicolinic acid (32.5 g, 153 mmol) in dioxane (550 mL) were added successively 4-(4,4,5,5-tetramethyl-[1,3,2]dioxaborolan-2-yl)-3,6-dihydro-2H-pyridine-1-carboxylic acid tert-butyl ester (56.7 g, 183 mmol), bis(triphenylphosphine)palladium (II) chloride (5.53 g, 7.64 mmol) and aq. sol. sodium carbonate (49.1 g in 80 mL of water, 459 mmol) at room temperature. After stirring 3 h at 110° C., the reaction mixture was cooled, and the solvent was evaporated. The resulting yellow oil was dissolved in ethyl acetate (100 mL) and washed with brine (100 mL). The organic layer was dried over sodium sulfate, filtered, and evaporated under reduced pressure. The crude mixture was purified by column chromatography on silica gel (ethylacetate/heptane 3:7) to give 3,6-dihydro-2H-[4,4']bipyridinyl-1,2'-dicarboxylic acid 1-tert-butyl ester. LC-MS: Rt=0.68 min; MS: m/z=305 (M+1), 306 (M+2).

b) Preparation of 2'-[(R)-(1,2,3,4-tetrahydronaphthalen-1-yl)carbamoyl]-3,6-dihydro-2H-[4,4']bipyridinyl-1-carboxylic acid tert-butyl ester Ethyldiisopropylamine (5.3 g, 41 mmol) and HATU (7.8 g, 20 mmol) and were added consecutively at 0° C. to a suspension of 3,6-dihydro-2H-[4,4']bipyridinyl-1,2'-dicarboxylic acid 1-tert-butyl ester (5.0 g, 16 mmol) in 80 ml of N,N-dimethylformamide. This mixture was stirred for 20 min at room temperature, then cooled again to 0° C. and a solution of R-(−)-1,2,3,4-tetrahydro-1-naphthylamine (3.0 g, 20 mmol) in 20 ml of N,N-dimethylformamide was slowly added. The reaction mixture was stirred for 16 h at room temperature. Subsequently the solvent was removed in vacuo, the remaining oil dissolved in ethyl acetate and washed with a saturated aqueous sodium bicarbonate solution, 0.5 N hydrochloric acid and brine. The organic layer was dried over sodium sulfate and evaporated, the residue was purified by column chromatography on silica gel (ethylacetate/cyclohexane 3:7) to give 2'-[(R)-(1,2,3,4-tetrahydronaphthalen-1-yl)carbamoyl]-3,6-dihydro-2H-[4,4']bipyridinyl-1-carboxylic acid tert-butyl ester. LC-MS: Rt=2.14 min; MS: m/z=434 (M+1), 435 (M+2).

c) Preparation of 2'-(R)-(1,2,3,4-tetrahydronaphthalen-1-ylcarbamoyl)-3,4,5,6-tetrahydro-2H-[4,4']bipyridinyl-1-carboxylic acid tert-butyl ester A solution of 2'-[(R)-(1,2,3,4-tetrahydronaphthalen-1-yl)carbamoyl]-3,6-dihydro-2H-[4,4']bipyridinyl-1-carboxylic acid tert-butyl ester (7.0 g, 16 mmol) in ethanol (62 mL) was pumped through a Pd/C cartridge using H-Cube apparatus (20° C., 10 bar, 2 mL/min.). The solvent was then evaporated under reduced pressure to give 2'-(R)-(-1,2,3,4-tetrahydronaphthalen-1-ylcarbamoyl)-3,4,5,6-tetrahydro-2H-[4,4']bipyridinyl-1-carboxylic acid tert-butyl ester which could be used in the next step without further purification. LC-MS: Rt=2.10 min; MS: m/z=436 (M+1), 437 (M+2).

d) Preparation of 1',2',3',4',5',6'-hexahydro-[4,4']bipyridinyl-2-carboxylic acid (R)-(1,2,3,4-tetrahydro-naphthalen-1-yl)-amide To a solution of 2'-(R)-(-1,2,3,4-tetrahydronaphthalen-1-ylcarbamoyl)-3,4,5,6-tetrahydro-2H-[4,4']bipyridinyl-1-carboxylic acid tert-butyl ester (6.7 g, 15 mmol) in a mixture of dichloromethane (80 ml) and methanol (80 ml) was added 120 ml of 1.25 M hydrochloric acid solution in ethanol. The reaction mixture was stirred for 16 h at room temperature. Subsequently the solvent was removed in vacuo, the residue crystallized from diethyl ether, delivering 1',2',3',4',5',6'-hexahydro-[4,4']bipyridinyl-2-carboxylic acid (R)-(1,2,3,4-tetrahydro-naphthalen-1-yl)-amide which could be used in the next step without further purification. LC-MS: Rt=0.96 min; MS: m/z=336 (M+1), 337 (M+2).

e) Preparation of 1'-[2-(3,5-bis-difluoromethyl-pyrazol-1-yl)-acetyl]-1',2',3',4',5',6'-hexahydro-[4,4']bipyridinyl-2-carboxylic acid (R)-(1,2,3,4-tetrahydronaphthalen-1-yl)-amide (compound A-1.2)

To solution of 2-[3,5-bis(difluoromethyl)pyrazol-1-yl] acetic acid (3.0 g, 13 mmol) in 20 ml of acetonitrile were added consecutively at room temperature triethylamine (3.5 g, 35 mmol), N'-(3-dimethylaminoprpoyl)-N-ethyl-carbodiimide (2.7 g, 14 mmol) and 1-hydroxy-7-azabenzotriazole (1.9 g, 14 mmol). This mixture was stirred for 15 min at room temperature, then 1',2',3',4',5',6'-hexahydro-[4,4']bipyridinyl-2-carboxylic acid (R)-(1,2,3,4-tetrahydro-naphthalen-1-yl)-amide (4.3 g, 12 mmol) were added to it. The reaction mixture was stirred for 16 h at room temperature, then concentrated in vacuo. The residue was taken up in ethyl acetate and washed with water, 0.5 M hydrochloric acid and brine. The organic phase was dried over sodium sulfate and evaporated. The remainder was purified by column chromatography on silica gel (ethylacetate/cyclohexane 1:1) to give 1'-[2-(3,5-bis-difluoromethyl-pyrazol-1-yl)-acetyl]-1',2',3',4',5',6'-hexahydro-[4,4']bipyridinyl-2-carboxylic acid (R)-(1,2,3,4-tetrahydronaphthalen-1-yl)-amide (compound A-1.2). LC-MS: Rt=1.88 min; MS: m/z=544 (M+1), 545 (M+2). M.p. 136-139° C.

Throughout this description, temperatures are given in degrees Celsius and "m.p." means melting point. LC/MS means Liquid Chromatography Mass Spectroscopy and the description of the apparatus and the method is: (HP 1100 HPLC from Agilent, Phenomenex Gemini C18, 3 ⌈ m particle size, 110 Angström, 30×3 mm column, 1.7 mL/min., 60° C., H$_2$O+0.05% HCOOH (95%)/CH$_3$CN/MeOH 4:1+ 0.04% HCOOH (5%)-2 min.-CH$_3$CN/MeOH 4:1+0.04% HCOOH (5%)-0.8 min., ZQ Mass Spectrometer from Waters, ionization method: electrospray (ESI), Polarity: positive ions, Capillary (kV) 3.00, Cone (V) 30.00, Extractor (V) 2.00, Source Temperature (° C.) 100, Desolvation Temperature (° C.) 250, Cone Gas Flow (L/Hr) 50, Desolvation Gas Flow (L/Hr) 400)).

TABLE 1

| Compound No. | Structural formula | Compound | LC/MS |
| --- | --- | --- | --- |
| A-1.1 | | 1'-[2-(3-difluoromethyl-5-methyl-pyrazol-1-yl)-acetyl]-1',2',3',4',5',6'-hexahydro-[4,4']bipyridinyl-2-carboxylic acid (R)-(1,2,3,4-tetrahydro-naphthalen-1-yl)-amide | Rt = 1.08 min; MS: m/z = 508 (M + 1) |

This table gives analytical data (LC/MS) for compounds of the invention.

TABLE 2

| Compound No. | Structural formula | Compound | m.p. (° C.) |
|---|---|---|---|
| A-1.2 | | 1'-[2-(3,5-bis-difluoromethyl-pyrazol-1-yl)-acetyl]-1',2',3',4',5',6'-hexahydro-[4,4']bipyridinyl-2-carboxylic acid (R)-(1,2,3,4-tetrahydro-naphthalen-1-yl)-amide | 136-139 |
| A-1.3 | | 1'-[2-(5-cyclopropyl-3-difluoromethyl-pyrazol-1-yl)-acetyl]-1',2',3',4',5',6'-hexahydro-[4,4']bipyridinyl-2-carboxylic acid (R)-(1,2,3,4-tetrahydro-naphthalen-1-yl)-amide | 75-78 |
| A-1.4 | | 1'-[2-(5-methyl-3-trifluoromethyl-pyrazol-1-yl)-acetyl]-1',2',3',4',5',6'-hexahydro-[4,4']bipyridinyl-2-carboxylic acid (R)-(1,2,3,4-tetrahydro-naphthalen-1-yl)-amide | 82-86 |
| A-1.5 | | 1'-[2-(3,5-bis-trifluoromethyl-pyrazol-1-yl)-acetyl]-1',2',3',4',5',6'-hexahydro-[4,4']bipyridinyl-2-carboxylic acid (R)-(1,2,3,4-tetrahydro-naphthalen-1-yl)-amide | 82-84 |
| A-1.6 | | 1'-[2-(5-cyclopropyl-3-trifluoromethyl-pyrazol-1-yl)-acetyl]-1',2',3',4',5',6'-hexahydro-[4,4']bipyridinyl-2-carboxylic acid (R)-(1,2,3,4-tetrahydro-naphthalen-1-yl)-amide | 91-93 |

This table gives analytical data (melting point) for compounds of the invention.

The components (B) are known. Most of the components (B) are referred to hereinabove by a so-called "ISO common name" or another "common name" being used in individual cases or a trademark name.

The following preferred components (B) are included in "The Pesticide Manual" [The Pesticide Manual—A World Compendium; Fourteenth Edition; Editor: C. D. S. Tomlin; The British Crop Protection Council], they are described therein under the entry number given in round brackets. For example, the compound "abamectin" is described under entry number (1). If the designation is not a "common name", the IUPAC name, the IUPAC/Chemical Abstracts name, a "chemical name", a "traditional name", a "compound name" or a "development code" is used or, if neither one of those designations nor a "common name" is used, an "alternative name" is employed Acibenzolar-S-methyl (7), azoxystrobin (47), benthiavalicarb (69), chlorothalonil (146), cyazofamid (188), cymoxanil (203), cyproconazole (210), cyprodinil (211), difenoconazole (253), dimethomorph (271), dithianon (289), epoxiconazole (310), famoxadone (334), fenamidone (337), fluazinam (374), fludioxonil (380), flumorph (389), flupicolide (391), folpet (412), fosetyl-Al (419), iprovalicarb (485), mancozeb (513), mandipropamid (514), mefenoxam (metalaxyl-M) (536), metalaxyl (535), propamocarb (689), propiconazole (696), prothioconazole (705), pyraclostrobin (710) and trifloxystrobin (854).

Ametoctradin and amisulbrom are described by H. Sauter, "Strobilurins and other Complex III inhibitors" in "Modern Crop Protection Compounds", ed. by W. Krämer, U. Schirmer, P. Jeschke and M. Witschel, Wiley-VCH, Weinheim, 2012, pp. 584-627.

Bixafen, fluxapyroxad, fluopyram, isopyrazam, sedaxane and solatenol are described by H. Walter, "Pyrazole carboxamide fungicides inhibiting Succinate dehydrogenase" in "Bioactive Heterocyclic Compound Classes", edited by C. Lamberth and J. Dinges, Wiley-VCH, Weinheim, 2012, pp. 175-193.

Pyrimorph and valifenalate are described by U. Gisi, C. Lamberth, A. Mehl and T. Seitz, "Carboxylic acid amide (CAA) fungicides" in "Modern Crop Protection Compounds", ed. by W. Krämer, U. Schirmer, P. Jeschke and M. Witschel, Wiley-VCH, Weinheim, 2012, pp. 807-830.

3-Difluoromethyl-1-methyl-1H-pyrazole-4-carboxylic acid methoxy-[1-methyl-2-(2,4,6-trichlorophenyl)-ethyl]-amide is disclosed and prepared in WO2010/063700, example P3.

Examples of especially suitable compounds as component (B) are compounds selected from the following group P:

Group P: especially suitable compounds as component (B) in the compositions according to the invention:

a strobilurin fungicide selected from azoxystrobin, coumoxystrobin, dimoxystrobin, enoxastrobin, flufenoxystrobin, fluoxastrobin, kresoxim-methyl, mandestrobin, metominostrobin, orysastrobin, picoxystrobin, pyraclostrobin, pyrametostrobin, pyraoxystrobin, triclopyricarb and trifloxystrobin;

an azole fungicide selected from azaconazole, bromuconazole, cyproconazole, difenoconazole, diniconazole, diniconazole-M, epoxiconazole, fenbuconazole, fluquinconazole, flusilazole, flutriafol, hexaconazole, imazalil, imibenconazole, ipconazole, metconazole, myclobutanil, oxpoconazole, pefurazoate, penconazole, prochloraz, propiconazole, prothioconazole, simeconazole, tebuconazole, tetraconazole, triadimefon, triadimenol, triflumizole, triticonazole, diclobutrazol, etaconazole, furconazole, furconazole-cis and quinconazole;

a morpholine fungicide selected from aldimorph, dodemorph, fenpropimorph, tridemorph, fenpropidin, spiroxamine, piperalin;

an anilinopyrimidine fungicide selected from cyprodinil, mepanipyrim and pyrimethanil;

a carboxamide fungicide selected from bixafen, boscalid, carboxin, fenfuram, fluopyram, fluxapyroxad, furametpyr, isopyrazam, oxycarboxin, penflufen, penthiopyrad, sedaxane, solatenol, thifluzamide and 3-difluoromethyl-1-methyl-1H-pyrazole-4-carboxylic acid methoxy-[1-methyl-2-(2,4,6-trichlorophenyl)-ethyl]-amide;

a phenylamide fungicide selected from the group of benalaxyl, furalaxyl, mefenoxam (metalaxyl-M), metalaxyl, ofurace and oxadixyl;

a carboxylic acid amide fungicide selected from the group of benthiavaliacrb, dimethomorph, flumorph, iprovalicarb, mandipropamid, pyrimorph and valifenalate;

a fungicide selected from the group consisting of etridiazole, fluazinam, benalaxyl-M, dodicin, N'-(2,5-dimethyl-4-phenoxy-phenyl)-N-ethyl-N-methyl-formamidine, N'-[4-(4,5-dichloro-thiazol-2-yloxy)-2,5-dimethyl-phenyl]-N-ethyl-N-methyl-formamidine, N'-[4-[[3-[(4-chlorophenyl)methyl]-1,2,4-thiadiazol-5-yl]oxy]-2,5-dimethyl-phenyl]-N-ethyl-N-methyl-formamidine, ethirimol, 3'-chloro-2-methoxy-N-[(3RS)-tetrahydro-2-oxofuran-3-yl]acet-2',6'-xylidide, dithianon, aureofungin, blasticidin-S, biphenyl, chloroneb, dicloran, hexachlorobenzene, quintozene, tecnazene, tolclofos-methyl, metrafenone, 2,6-dichloro-N-(4-trifluoromethylbenzyl)-benzamide, fluopicolide, tioxymid, flusulfamide, benomyl, carbendazim, carbendazim chlorhydrate, chlorfenazole, fuberidazole, thiabendazole, thiophanate-methyl, chlobenthiazone, probenazole, acibenzolar, bethoxazin, pyriofenone, pyribencarb, butylamine, 3-iodo-2-propinyl n-butylcarbamate, iodocarb, isopropanyl butylcarbamate, picarbutrazox, polycarbamate, propamocarb, tolprocarb, 3-(difluoromethyl)-N-(7-fluoro-1,1,3,3-tetramethyl-indan-4-yl)-1-methyl-pyrazole-4-carboxamide, diclocymet, N-[(5-chloro-2-isopropyl-phenyl)methyl]-N-cyclopropyl-3-(difluoromethyl)-5-fluoro-1-methyl-pyrazole-4-carboxamide, N-cyclopropyl-3-(difluoromethyl)-5-fluoro-N-[(2-isopropylphenyl)methyl]-1-methyl-pyrazole-4-carboxamide, carpropamid, chlorothalonil, oxine-copper, cymoxanil, phenamacril, cyazofamid, flutianil, thicyofen, chlozolinate, iprodione, procymidone, vinclozolin, bupirimate, dinocton, dinopenton, dinobuton, dinocap, meptyldinocap, diphenylamine, phosdiphen, 2,6-dimethyl-[1,4]dithiino[2,3-c:5,6-c']dipyrrole-1,3,5,7(2H,6H)-tetraone, etem, ferbam, mancozeb, maneb, metam, metiram, metiram-zinc, nabam, propineb, thiram, vapam, zineb, ziram, dithioether, isoprothiolane, ethaboxam, fosetyl, phosetyl-Al, methyl bromide, methyl iodide, methyl isothiocyanate, cyclafuramid, validamycin, streptomycin, (2RS)-2-bromo-2-(bromomethyl)glutaronitrile, dodine, doguadine, guazatine, iminoctadine, iminoctadine triacetate, 2,4-D, 2,4-DB, kasugamycin, dimethirimol, fenhexamid, hymexazole, imazalil sulphate, fenamidone, Bordeaux mixture, calcium polysulfide, copper acetate, copper carbonate, copper hydroxide, copper naphthenate, copper oleate, copper oxychloride, copper oxyquinolate, copper silicate, copper sulphate, copper tallate, cuprous oxide, sulphur, carbaryl, phthalide, dingjunezuo, oxathiapiprolin, fluoroimide, KSF-1002, benzamorf, diethofencarb, fentin acetate, fentin hydroxide, drazoxolon, famoxadone, m-phenylphenol, p-phenylphenol, tribromphenol, 2-[2-[(7,8-difluoro-2- methyl-3-quinolyl)oxy]-6-fluoro-phenyl]propan-2-ol, 2-[2-fluoro-6-[(8-fluoro-2-methyl-3-quinolyl)oxy]phenyl]propan-2-ol, cyflufenamid, flutolanil, mepronil, isofetamid, fenpiclonil, fludioxonil, pencycuron, edifenphos, iprobenfos, pyrazophos, phosphorus acids, tecloftalam, captafol, captan, ditalimfos, CAS 517875-34-2, triforine, osthol, 1-methylcyclopropene, 4-CPA, dichlorprop, dimethipin, endothal, flumetralin, forchlorfenuron, gibberellic acid, gibberellins, hymexazol, maleic hydrazide, naphthalene acetamide, paclobutrazol, prohexadione, prohexadione-calcium, thidiazuron, tribufos, trinexapac, uniconazole, α-naphthalene acetic acid, polyoxin D, BLAD, chitosan, fenoxanil, folpet, 3-(difluoromethyl)-N-methoxy-1-methyl-N-[1-methyl-2-(2,4,6-trichlorophenyl)ethyl]pyrazole-4-carboxamide, benzovindiflupyr, fenpyrazamine, diclomezine, pyrifenox, diflumetorim, fenarimol, 5-fluoro-2-(p-tolylmethoxy)pyrimidin-4-amine, ferimzone, dimetachlone, pyroquilon, proquinazid, ethoxyquin, quinoxyfen, 4,4,5-trifluoro-3,3-dimethyl-1-(3-quinolyl)isoquinoline, 4,4-difluoro-3,3-dimethyl-1-(3-quinolyl)isoquinoline, 5-fluoro-3,3,4,4-tetramethyl-1-(3-quinolyl)isoquinoline, 9-fluoro-2,2-dimethyl-5-(3-quinolyl)-3H-1,4-benzoxazepine, tebufloquin, oxolinic acid, chinomethionate, (E)-N-methyl-2-[2-(2,5-dimethylphenoxymethyl) phenyl]-2-methoxy-iminoacetamide, enestroburin, fenamistrobin, amisulbrom, dichlofluanid, tolylfluanid, but-3-ynyl N-[6-[[(Z)-[(1-methyltetrazol-5-yl)-phenyl-methylene]amino]oxymethyl]-2-pyridyl]carbamate, dazomet, benthiazole, silthiofam, zoxamide, anilazine, tricyclazole, (.+−.)-cis-1-(4-chlorophenyl)-2-(1H-1,2,4-triazol-1-yl)-cycloheptanol, 1-(5-bromo-2-pyridyl)-2-(2,4-difluorophenyl)-1,1-difluoro-3-(1,2,4-triazol-1-yl)propan-2-ol, 2-(1-tert-butyl)-1-(2-chlorophenyl)-3-(1,2,4-triazol-1-yl)-propan-2-ol, bitertanol, climbazole, dimetconazole, triazoxide, 2-[[(1R,5S)-5-[(4-fluorophenyl)methyl]-1-hydroxy-2,2-dimethyl-cyclopentyl] methyl]-4H-1,2,4-triazole-3-thione, 2-[[3-(2-chlorophenyl)-2-(2,4-difluorophenyl)oxiran-2-yl]methyl]-4H-1,2,4-triazole-3-thione, flupicolide, and ametoctradin, a plant-bioregulator selected from the group consisting of acibenzolar-S-methyl, chlormequat chloride, ethephon, isotianil, mepiquat chloride, tiadinil and trinexapc-ethyl;

an insecticide selected from the group consisting of abamectin, acequinocyl, acetamiprid, acrinathrin, alanycarb, allethrin, alpha-cypermethrin, alphamethrin, amidoflumet, azadirachtin, azocyclotin, *bacillus firmus, bacillus thuringiensis*, bensultap, benzoximate, betacyfluthrin, bifenazate, binapacryl, bioallethrin, bioallethrin s)-cyclopentylisomer, bioresmethrin, biphenthrin, brofluthrinate, bromophos-ethyl, buprofezine, cadusafos, carbaryl, carbosulfan, cartap, chlorantraniliprole, chlorfenapyr, chromafenozide, cloethocarb, clothianidin, cyantraniliprole, cyclaniliprole, cycloprothrin, cycloxaprid, cyenopyrafen, cyflumetofen, cyfluthrin, cyhalothrin, cypermethrin, cyphenothrin, cyromazine, deltamethrin, demeton-s-methyl, diafenthiuron, dialifos, dibrom, diflovidazine, diflubenzuron, dinactin, dinocap, dinotefuran, d-limonene, emamectin, empenthrin, esfenvalerate, ethion, ethiprole, etofenprox, etoxazole, famphur, fenazaquin, fenfluthrin, fenobucarb, fenoxycarb, fenpropathrin, fenpyroximate, fenvalerate, fipronil, flometoquin, flonicamid, floupyram, fluacrypyrim, fluazuron, flubendiamide, flucythrinate, fluensulfone, flufenerim, flufenprox, flufiprole, fluhexafon, flumethrin, flupyradifuron, fluvalinate, fosthiazate, gamma-cyhalothrin, gossyplure, guadipyr, halofenozide, halofenprox, harpin, hexythiazox, hydramethylnon, imicyafos, imidacloprid, imiprothrin, indoxacarb, iodomethane, isothioate, ivermectin, lambda-cyhalothrin, lepimectin, lufenuron, metaflumizone, metaldehyde, methomyl, methoxyfenozide, metofluthrin, milbemectin, niclosamide, nitenpyram, oxamyl, parathion-ethel, pasteuria nishizawae, p-cymene, permethrin, phenothrin, phosphocarb, piperonylbutoxide, pirimicarb, pirimiphos-ethyl, polyhedrosis virus, prallethrin, profenofos, profenofos, propargite, propetamphos, protrifenbute, pyflubumide, pymetrozine, pyraclofos, pyrafluprole, pyrethrum, pyridaben, pyridalyl, pyrifluquinazon, pyrimidifen, pyriprole, pyriproxyfen, selamectin, silafluofen, spinetoram, spinosad, spirodiclofen, spiromesifen, spirotetramat, sulfoxaflor, tebufenozide, tebufenpyrad, tefluthrin, terpenoid blends, terpenoids, tetradiphon, tetramethrin, tetranactin, tetraniliprole, theta-cypermethrin, thiacloprid, thiamethoxam, thiodicarb, tolfenpyrad, transfluthrin, trichlorfon, triflumezopyrim, zeta-cypermethrin and α-terpinene; and glyphosate.

Further examples of especially suitable compounds as component (B) are compounds selected from the following group Q:

Group Q: especially suitable compounds as component (B) in the compositions according to the invention:

a strobilurin fungicide selected from the group consisting of azoxystrobin, pyraclostrobin and trifloxystrobin;

an azole fungicide selected from the group consisting of cyproconazole, difenoconazole, epoxiconazole, propiconazole and prothioconazole;

an anilinopyrimidine fungicide selected from cyprodinil;

a carboxamide fungicide selected from bixafen, fluopyram, fluxapyroxad, isopyrazam, sedaxane, solatenol and 3-difluoromethyl-1-methyl-1H-pyrazole-4-carboxylic acid methoxy-[1-methyl-2-(2,4,6-trichlorophenyl)-ethyl]-amide.

a phenylamide fungicide selected from mefenoxam (metalaxyl-M) and metalaxyl;

a carboxylic acid amide fungicide selected from benthiavalicarb, dimethomorph, flumorph, iprovalicarb and mandipropamid, pyrimorph and valifenalate;

a fungicide selected from the group consisting of acibenzolar-S-methyl, ametoctradin, amisulbrom, chlorothalonil, copper, cyazofamid, cymoxanil, disodium phosphonate, dithianon, famoxadone, fenamidone, fluazinam, fludioxonil, flupicolide, folpet, fosetyl-Al, mancozeb and propamocarb.

Throughout this document the expression "composition" stands for the various mixtures or combinations of components (A) and (B), for example in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the components (A) and (B) is not essential for working the present invention.

The compositions according to the invention may also comprise more than one of the active components (B), if, for example, a broadening of the spectrum of phytopathogenic disease control is desired. For instance, it may be advantageous in the agricultural practice to combine two or three components (B) with component (A). An example is a composition comprising a compound of formula (I), azoxystrobin and mandipropamid.

Further examples for compositions according to the present invention which comprise three active ingredients are defined as embodiments E1, E2 and E3:

Embodiment E1

The term "TX1" means: "the compound A-1.1+ a compound selected from the group P"

Azoxystrobin+TX1, coumoxystrobin+TX1, dimoxystrobin+TX1, enoxastrobin+TX1, flufenoxystrobin+TX1, fluoxastrobin+TX1, kresoxim-methyl+TX1, mandestrobin+TX1, metominostrobin+TX1, orysastrobin+TX1, picoxystrobin+TX1, pyraclostrobin+TX1, pyrametostrobin+TX1, pyraoxystrobin+TX1, triclopyricarb+TX1, trifloxystrobin+TX1, azaconazole+TX1, bromuconazole+TX1, cyproconazole+TX1, difenoconazole+TX1, diniconazole+TX1, diniconazole-M+TX1, epoxiconazole+TX1, fenbuconazole+TX1, fluquinconazole+TX1, flusilazole+TX1, flutriafol+TX1, hexaconazole+TX1, imazalil+TX1, imibenconazole+TX1, ipconazole+TX1, metconazole+TX1, myclobutanil+TX1, oxpoconazole+TX1, pefurazoate+TX1, penconazole+TX1, prochloraz+TX1, propiconazole+TX1, prothioconazole+TX1, simeconazole+TX1, tebuconazole+TX1, tetraconazole+TX1, triadimefon+TX1, triadimenol+TX1, triflumizole+TX1, triticonazole+TX1, diclobutrazol+TX1, etaconazole+TX1, furconazole+TX1, furconazole-cis+TX1, quinconazole+TX1, aldimorph+TX1, dodemorph+TX1, fenpropimorph+TX1, tridemorph+TX1, fenpropidin+TX1, spiroxamine+TX1, piperalin+TX1, cyprodinil+TX1, mepanipyrim+TX1, pyrimethanil+TX1, bixafen+TX1, boscalid+TX1, carboxin+TX1, fenfuram+TX1, fluopyram+TX1, fluxapyroxad+TX1, furametpyr+TX1, isopyrazam+TX1, oxycarboxin+TX1, penflufen+TX1, penthiopyrad+TX1, sedaxane+TX1, solatenol+TX1, thifluzamide+TX1, 3-difluoromethyl-1-methyl-1H-pyrazole-4-carboxylic acid methoxy-[1-methyl-2-(2,4,6-trichlorophenyl)-ethyl]-amide+TX1, benalaxyl+TX1, furalaxyl+TX1, mefenoxam (metalaxyl-M)+TX1, metalaxyl+TX1, ofurace+TX1, oxadixyl+TX1, benthiavalicarb+TX1, dimethomorph+TX1, flumorph+TX1, iprovalicarb+TX1, mandipropamid+TX1, pyrimorph+TX1, valifenalate+TX1, ametoctradin+TX1, amisulbrom+TX1, benomyl+TX1, bitertanol+TX1, captan+TX1, carpropamid+TX1, chlorothalonil+TX1, copper+TX1, cyazofamid+TX1, cyflufenamid+TX1, cymoxanil+TX1, diethofencarb+TX1, dithianon+TX1, famoxadone+TX1, fenamidone+TX1, fenhexamide+TX1, fenoxycarb+TX1, fenpiclonil+TX1, fluazinam+TX1, fludioxonil+TX1, flupicolide+TX1, flutolanil+TX1, folpet+TX1, guazatine+TX1, hymexazole+TX1, iprodione+TX1, mancozeb+TX1, metrafenone+TX1, nuarimol+TX1, oxathiapiprolin+TX1, paclobutrazol+TX1, pencycuron+TX1, procymidone+TX1, proquinazid+TX1, pyribencarb+TX1, pyroquilon+TX1, quinoxyfen+TX1, silthiofam+TX1, sulfur+TX1, thiabendazole+TX1, thiram+TX1, triazoxide+TX1, tricyclazole+TX1, zoxamide+TX1, acibenzolar-S-methyl+TX1, chlormequat chloride+TX1, ethephon+TX1, isotianil+TX1, mepiquat chloride+TX1, tiadinil+TX1, trinexapac-ethyl+TX1, abamectin+TX1, clothianidin+TX1, emamectin benzoate+TX1, imidacloprid+TX1, tefluthrin+TX1, thiamethoxam+TX1, chlorantraniliprole+TX1, cyantraniliprole+TX1, fosetyl-Al+TX1, propamocarb+TX1 and glyphosate+TX1.

Embodiment E2

The term "TX2" means: "the compound A-1.2+ a compound selected from the group P".

Azoxystrobin+TX2, coumoxystrobin+TX2, dimoxystrobin+TX2, enoxastrobin+TX2, flufenoxystrobin+TX2, fluoxastrobin+TX2, kresoxim-methyl+TX2, mandestrobin+TX2, metominostrobin+TX2, orysastrobin+TX2, picoxystrobin+TX2, pyraclostrobin+TX2, pyrametostrobin+TX2, pyraoxystrobin+TX2, triclopyricarb+TX2, trifloxystrobin+TX2, azaconazole+TX2, bromuconazole+TX2, cyproconazole+TX2, difenoconazole+TX2, diniconazole+TX2, diniconazole-M+TX2, epoxiconazole+TX2, fenbuconazole+TX2, fluquinconazole+TX2, flusilazole+TX2, flutriafol+TX2, hexaconazole+TX2, imazalil+TX2, imibenconazole+TX2, ipconazole+TX2, metconazole+TX2, myclobutanil+TX2, oxpoconazole+TX2, pefurazoate+TX2, penconazole+TX2, prochloraz+TX2, propiconazole+TX2, prothioconazole+TX2, simeconazole+TX2, tebuconazole+TX2, tetraconazole+TX2, triadimefon+TX2, triadimenol+TX2, triflumizole+TX2, triticonazole+TX2, diclobutrazol+TX2, etaconazole+TX2, furconazole+TX2, furconazole-cis+TX2, quinconazole+TX2, aldimorph+TX2, dodemorph+TX2, fenpropimorph+TX2, tridemorph+TX2, fenpropidin+TX2, spiroxamine+TX2, piperalin+TX2, cyprodinil+TX2, mepanipyrim+TX2, pyrimethanil+TX2, bixafen+TX2, boscalid+TX2, carboxin+TX2, fenfuram+TX2, fluopyram+TX2, fluxapyroxad+TX2, furametpyr+TX2, isopyrazam+TX2, oxycarboxin+TX2, penflufen+TX2, penthiopyrad+TX2, sedaxane+TX2, solatenol+TX2, thifluzamide+TX2, 3-difluoromethyl-1-methyl-1H-pyrazole-4-carboxylic acid methoxy-[1-methyl-2-(2,4,6-trichlorophenyl)-ethyl]-amide+TX2, benalaxyl+TX2, furalaxyl+TX2, mefenoxam (metalaxyl-M)+TX2, metalaxyl+TX2, ofurace+TX2, oxadixyl+TX2, benthiavalicarb+TX2, dimethomorph+TX2, flumorph+TX2, iprovalicarb+TX2, mandipropamid+TX2, pyrimorph+TX2, valifenalate+TX2, ametoctradin+TX2, amisulbrom+TX2, benomyl+TX2, bitertanol+TX2, captan+TX2, carpropamid+TX2, chlorothalonil+TX2, copper+TX2, cyazofamid+TX2, cyflufenamid+TX2, cymoxanil+TX2, diethofencarb+TX2, dithianon+TX2, famoxadone+TX2, fenamidone+TX2, fenhexamide+TX2, fenoxycarb+TX2, fenpiclonil+TX2, fluazinam+TX2, fludioxonil+TX2, flupicolide+TX2, flutolanil+TX2, folpet+TX2, guazatine+TX2, hymexazole+TX2, iprodione+TX2, mancozeb+TX2, metrafenone+TX2, nuarimol+TX2, oxathiapiprolin+TX1, paclobutrazol+TX2, pencycuron+TX2, procymidone+TX2, proquinazid+TX2, pyribencarb+TX2, pyroquilon+TX2, quinoxyfen+TX2, silthiofam+TX2, sulfur+TX2, thiabendazole+TX2, thiram+TX2, triazoxide+TX2, tricyclazole+TX2, zoxamide+TX2, acibenzolar-S-methyl+TX2, chlormequat chloride+TX2, ethephon+TX2, isotianil+TX2, mepiquat chloride+TX2, tiadinil+TX2, trinexapac-ethyl+TX2, abamectin+TX2, clothianidin+TX2, emamectin benzoate+TX2, imidacloprid+TX2, tefluthrin+TX2, thiamethoxam+TX2, chlorantraniliprole+TX2, cyantraniliprole+TX2, fosetyl-Al+TX2, propamocarb+TX2 and glyphosate+TX2.

Embodiment E3

The term "TX3" means: "the compound A-1.3+ a compound selected from the group P".

Azoxystrobin+TX3, coumoxystrobin+TX3, dimoxystrobin+TX3, enoxastrobin+TX3, flufenoxystrobin+TX3, fluoxastrobin+TX3, kresoxim-methyl+TX3, mandestrobin+TX3, metominostrobin+TX3, orysastrobin+TX3, picoxystrobin+TX3, pyraclostrobin+TX3, pyrametostrobin+TX3, pyraoxystrobin+TX3, triclopyricarb+TX3, trifloxystrobin+TX2, azaconazole+TX3, bromuconazole+TX3, cyproconazole+TX2, difenoconazole+TX3, diniconazole+TX3, diniconazole-M+TX3, epoxiconazole+TX3, fenbuconazole+TX3, fluquinconazole+TX3, flusilazole+TX3, flutriafol+TX3, hexaconazole+TX3, imazalil+TX3, imibenconazole+TX3, ipconazole+TX3, metconazole+TX3, myclobutanil+

TX3, oxpoconazole+TX3, pefurazoate+TX3, penconazole+TX3, prochloraz+TX3, propiconazole+TX3, prothioconazole+TX3, simeconazole+TX3, tebuconazole+TX3, tetraconazole+TX3, triadimefon+TX3, triadimenol+TX3, triflumizole+TX3, triticonazole+TX3, diclobutrazol+TX3, etaconazole+TX3, furconazole+TX3, furconazole-cis+TX3, quinconazole+TX3, aldimorph+TX3, dodemorph+TX3, fenpropimorph+TX3, tridemorph+TX3, fenpropidin+TX3, spiroxamine+TX3, piperalin+TX3, cyprodinil+TX3, mepanipyrim+TX3, pyrimethanil+TX3, bixafen+TX3, boscalid+TX3, carboxin+TX3, fenfuram+TX3, fluopyram+TX3, fluxapyroxad+TX3, furametpyr+TX3, isopyrazam+TX3, oxycarboxin+TX3, penflufen+TX3, penthiopyrad+TX3, sedaxane+TX3, solatenol+TX3, thifluzamide+TX3, 3-difluoromethyl-1-methyl-1H-pyrazole-4-carboxylic acid methoxy-[1-methyl-2-(2,4,6-trichlorophenyl)-ethyl]-amide+TX3, benalaxyl+TX3, furalaxyl+TX3, mefenoxam (metalaxyl-M)+TX3, metalaxyl+TX3, ofurace+TX3, oxadixyl+TX3, benthiavalicarb+TX3, dimethomorph+TX3, flumorph+TX3, iprovalicarb+TX3, mandipropamid+TX3, pyrimorph+TX3, valifenalate+TX3, ametoctradin+TX3, amisulbrom+TX3, benomyl+TX3, bitertanol+TX3, captan+TX3, carpropamid+TX3, chlorothalonil+TX3, copper+TX3, cyazofamid+TX3, cyflufenamid+TX3, cymoxanil+TX3, diethofencarb+TX3, dithianon+TX3, famoxadone+TX3, fenamidone+TX3, fenhexamide+TX3, fenoxycarb+TX3, fenpiclonil+TX3, fluazinam+TX3, fludioxonil+TX3, flupicolide+TX3, flutolanil+TX3, folpet+TX3, guazatine+TX3, hymexazole+TX3, iprodione+TX3, mancozeb+TX3, metrafenone+TX3, nuarimol+TX3, oxathiapiprolin+TX3, paclobutrazol+TX3, pencycuron+TX3, procymidone+TX3, proquinazid+TX3, pyribencarb+TX3, pyroquilon+TX3, quinoxyfen+TX3, silthiofam+TX3, sulfur+TX3, thiabendazole+TX3, thiram+TX3, triazoxide+TX3, tricyclazole+TX3, zoxamide+TX3, acibenzolar-S-methyl+TX3, chlormequat chloride+TX3, ethephon+TX3, isotianil+TX3, mepiquat chloride+TX3, tiadinil+TX3, trinexapac-ethyl+TX3, abamectin+TX3, clothianidin+TX3, emamectin benzoate+TX4, imidacloprid+TX3, tefluthrin+TX3, thiamethoxam+TX3, chlorantraniliprole+TX3, cyantraniliprole+TX3, fosetyl-Al+ TX3, propamocarb+TX3 and glyphosate+TX3.

The embodiments E1, E2 and E3 define compositions according to the present invention which comprise 3 active ingredients. In said embodiments, the mixing partner selected from the group P has to be different from the other described mixing partners. For example, the composition "cyproconazole+TX1" means compositions comprising as active ingredients cyproconazole, the compound A-1.1+ a compound selected from the group P. In said compositions, the compound selected from the group P is different from cyproconazole.

The following compositions are preferred:

A composition comprising (A) compound A-1.1 and (B) a compound selected from the group P. An example of such a composition is a composition comprising the compound A-1.1 and the first compound from the group P, which is azoxystrobin.

A composition comprising (A) compound A-1.1 and (B) a compound selected from the group Q. An example of such a composition is a composition comprising the compound A-1.1 and the second compound from the group Q, which is pyraclostrobin.

A composition comprising (A) compound A-1.1 and (B) a strobilurin fungicide.

A composition comprising (A) compound A-1.1 and (B) an azole fungicide.

A composition comprising (A) compound A-1.1 and (B) a morpholine fungicide.

A composition comprising (A) compound A-1.1 and (B) an anilinopyrimidine fungicide.

A composition comprising (A) compound A-1.1 and (B) a carboxamide fungicide

A composition comprising (A) compound A-1.1 and (B) a phenylamide fungicide

A composition comprising (A) compound A-1.1 and (B) a carboxylic acid amide fungicide A composition comprising (A) compound A-1.1 and (B) a glyphosate.

A composition comprising (A) 1'[2-(3-difluoromethyl-5-methyl-pyrazol-1-yl)-acetyl]-1',2',3',4',5',6'-hexahydro-[4,4']bipyridinyl-2-carboxylic acid (R)-(1,2,3,4-tetrahydronaphthalen-1-yl)-amide (compound A-1.1) and (B) a fungicide selected from acibenzolar-S-methyl, ametoctradin, amisulbrom, azoxystrobin, benthiavalicarb, bixafen, chlorothalonil, copper, cyazofamid, cymoxanil, disodium phosphonate, cyproconazole, cyprodinil, difenoconazole, dimethomorph, dithianon, epoxiconazole, famoxadone, fenamidone, fluazinam, fludioxonil, flumorph, flupicolide, fluxapyroxad, fluopyram, folpet, fosetyl-Al, iprovalicarb, isopyrazam, mancozeb, mandipropamid, mefenoxam, metalaxyl, propamocarb, propiconazole, prothioconazole, pyraclostrobin, pyrimorph, sedaxane, solatenol, trifloxystrobin, valifenalate and 3-difluoromethyl-1-methyl-1H-pyrazole-4-carboxylic acid methoxy-[1-methyl-2-(2,4,6-trichlorophenyl)-ethyl]amide.

A composition comprising (A) 1'-[2-(3-difluoromethyl-5-methyl-pyrazol-1-yl)-acetyl]-1',2',3',4',5',6'-hexahydro-[4,4']bipyridinyl-2-carboxylic acid (R)-(1,2,3,4-tetrahydronaphthalen-1-yl)-amide (compound A-1.1) and (B) a fungicide selected from acibenzolar-S-methyl, ametoctradin, amisulbrom, azoxystrobin, benthiavalicarb, chlorothalonil, copper, cyazofamid, cymoxanil, disodium phosphonate, dimethomorph, dithianon, famoxadone, fenamidone, fluazinam, flumorph, flupicolide, folpet, fosetyl-Al, iprovalicarb, isopyrazam, mancozeb, mandipropamid, mefenoxam, metalaxyl, pyraclostrobin, solatenol, trifloxystrobin and 3-difluoromethyl-1-methyl-1H-pyrazole-4-carboxylic acid methoxy-[1-methyl-2-(2,4,6-trichlorophenyl)-ethyl]-amide.

A composition comprising (A) compound A-1.2 and (B) a compound selected from the group P.

A composition comprising (A) compound A-1.2 and (B) a compound selected from the group Q.

A composition comprising (A) compound A-1.2 and (B) a strobilurin fungicide.

A composition comprising (A) compound A-1.2 and (B) an azole fungicide.

A composition comprising (A) compound A-1.2 and (B) a morpholine fungicide.

A composition comprising (A) compound A-1.2 and (B) an anilinopyrimidine fungicide.

A composition comprising (A) compound A-1.2 and (B) a carboxamide fungicide.

A composition comprising (A) compound A-1.2 and (B) a phenylamide fungicide

A composition comprising (A) compound A-1.2 and (B) a carboxylic acid amide fungicide A composition comprising (A) compound A-1.2 and (B) glyphosate.

A composition comprising (A) 1'-[2-(3,5-bis-difluoromethyl-pyrazol-1-yl)-acetyl]-1',2',3',4',5',6'-hexahydro-[4,4']bipyridinyl-2-carboxylic acid (R)-(1,2,3,4-tetrahydronaphthalen-1-yl)-amide (compound A-1.2) and (B) a fungicide selected from acibenzolar-S-methyl, ametoctradin, amisulbrom, azoxystrobin, benthiavalicarb, bixafen, chlorothalonil, copper, cyazofamid, cymoxanil, disodium phosphonate, cyproconazole, cyprodinil, difenoconazole, dimethomorph, dithianon, epoxiconazole, famoxadone, fenamidone, fluazinam, fludioxonil, flumorph, flupicolide, fluxapyroxad, fluopyram, folpet, fosetyl-Al, iprovalicarb, isopyrazam, mancozeb, mandipropamid, mefenoxam, metalaxyl, propamocarb, propiconazole, prothioconazole, pyraclostrobin, pyrimorph, sedaxane, solatenol, trifloxystrobin, valifenalate and 3-difluoromethyl-1-methyl-1H-pyrazole-4-carboxylic acid methoxy-[1-methyl-2-(2,4,6-trichlorophenyl)-ethyl]-amide.

A composition comprising (A) 1'-[2-(3,5-bis-difluoromethyl-pyrazol-1-yl)-acetyl]-1',2',3',4',5',6'-hexahydro-[4,4']bipyridinyl-2-carboxylic acid (R)-(1,2,3,4-tetrahydronaphthalen-1-yl)-amide (compound A-1.2) and (B) a fungicide selected from acibenzolar-S-methyl, ametoctradin, amisulbrom, azoxystrobin, benthiavalicarb, chlorothalonil, copper, cyazofamid, cymoxanil, disodium phosphonate, dimethomorph, dithianon, famoxadone, fenamidone, fluazinam, flumorph, flupicolide, folpet, fosetyl-Al, iprovalicarb, isopyrazam, mancozeb, mandipropamid, mefenoxam, metalaxyl, pyraclostrobin, solatenol, trifloxystrobin and 3-difluoromethyl-1-methyl-1H-pyrazole-4-carboxylic acid methoxy-[1-methyl-2-(2,4,6-trichlorophenyl)-ethyl]-amide.

A composition comprising (A) compound A-1.3 and (B) a compound selected from the group P.

A composition comprising (A) compound A-1.3 and (B) a compound selected from the group Q.

A composition comprising (A) compound A-1.3 and (B) a strobilurin fungicide.

A composition comprising (A) compound A-1.3 and (B) an azole fungicide.

A composition comprising (A) compound A-1.3 and (B) a morpholine fungicide.

A composition comprising (A) compound A-1.3 and (B) an anilinopyrimidine fungicide.

A composition comprising (A) compound A-1.3 and (B) a carboxamide fungicide.

A composition comprising (A) compound A-1.3 and (B) a phenylamide fungicide

A composition comprising (A) compound A-1.3 and (B) a carboxylic acid amide fungicide A composition comprising (A) compound A-1.3 and (B) a glyphosate.

A composition comprising (A) compound 1'-[2-(5-cyclopropyl-3-difluoromethyl-pyrazol-1-yl)-acetyl]-1',2',3',4',5',6'-hexa-hydro-[4,4']bi-pyridinyl-2-carboxylic acid (R)-(1,2,3,4-tetrahydronaphthalen-1-yl)-amide (compound A-1.3) and (B) a fungicide selected from acibenzolar-S-methyl, ametoctradin, amisulbrom, azoxystrobin, benthiavalicarb, bixafen, chlorothalonil, copper, cyazofamid, cymoxanil, disodium phosphonate, cyproconazole, cyprodinil, difenoconazole, dimethomorph, dithianon, epoxiconazole, famoxadone, fenamidone, fluazinam, fludioxonil, flumorph, flupicolide, fluxapyroxad, fluopyram, folpet, fosetyl-Al, iprovalicarb, isopyrazam, mancozeb, mandipropamid, mefenoxam, metalaxyl, propamocarb, propiconazole, prothioconazole, pyraclostrobin, pyrimorph, sedaxane, solatenol, trifloxystrobin, valifenalate and 3-difluoromethyl-1-methyl-1H-pyrazole-4-carboxylic acid methoxy-[1-methyl-2-(2,4,6-trichlorophenyl)-ethyl]-amide.

A composition comprising (A) compound 1'-[2-(5-cyclopropyl-3-difluoromethyl-pyrazol-1-yl)-acetyl]-1',2',3',4',5',6'-hexa-hydro-[4,4']bi-pyridinyl-2-carboxylic acid (R)-(1,2,3,4-tetrahydronaphthalen-1-yl)-amide (compound A-1.3) and (B) a fungicide selected from acibenzolar-S-methyl, ametoctradin, amisulbrom, azoxystrobin, benthiavalicarb, chlorothalonil, copper, cyazofamid, cymoxanil, disodium phosphonate, dimethomorph, dithianon, famoxadone, fenamidone, fluazinam, flumorph, flupicolide, folpet, fosetyl-Al, iprovalicarb, isopyrazam, mancozeb, mandipropamid, mefenoxam, metalaxyl, pyraclostrobin, solatenol, trifloxystrobin and 3-difluoromethyl-1-methyl-1H-pyrazole-4-carboxylic acid methoxy-[1-methyl-2-(2,4,6-trichlorophenyl)-ethyl]-amide.

A composition comprising (A) compound A-1.4 and (B) a compound selected from the group P.

A composition comprising (A) 1'-[2-(5-methyl-3-trifluoromethyl-pyrazol-1-yl)-acetyl]-1',2',3',4',5',6'-hexahydro-[4,4']bipyridinyl-2-carboxylic acid (R)-(1,2,3,4-tetrahydronaphthalen-1-yl)-amide (compound A-1.4) and (B) a fungicide selected from acibenzolar-S-methyl, ametoctradin, amisulbrom, azoxystrobin, benthiavalicarb, chlorothalonil, copper, cyazofamid, cymoxanil, disodium phosphonate, dimethomorph, dithianon, famoxadone, fenamidone, fluazinam, flumorph, flupicolide, folpet, fosetyl-Al, iprovalicarb, isopyrazam, mancozeb, mandipropamid, mefenoxam, metalaxyl, pyraclostrobin, solatenol, trifloxystrobin and 3-difluoromethyl-1-methyl-1H-pyrazole-4-carboxylic acid methoxy-[1-methyl-2-(2,4,6-trichlorophenyl)-ethyl]-amide.

A composition comprising (A) 1'-[2-(3,5-bis-trifluoromethyl-pyrazol-1-yl)-acetyl]-1',2',3',4',5',6'-hexahydro-[4,4']bipyridinyl-2-carboxylic acid (R)-(1,2,3,4-tetrahydronaphthalen-1-yl)-amide (compound A-1.5) and (B) a compound selected from the group P.

A composition comprising (A) compound A-1.5 and (B) a fungicide selected from acibenzolar-S-methyl, ametoctradin, amisulbrom, azoxystrobin, benthiavalicarb, chlorothalonil, copper, cyazofamid, cymoxanil, disodium phosphonate, dimethomorph, dithianon, famoxadone, fenamidone, fluazinam, flumorph, flupicolide, folpet, fosetyl-Al, iprovalicarb, isopyrazam, mancozeb, mandipropamid, mefenoxam, metalaxyl, pyraclostrobin, solatenol, trifloxystrobin and 3-difluoromethyl-1-methyl-1H-pyrazole-4-carboxylic acid methoxy-[1-methyl-2-(2,4,6-trichlorophenyl)-ethyl]-amide.

A composition comprising (A) compound A-1.6 and (B) a compound selected from the group P. A composition comprising (A) 1'-[2-(5-cyclopropyl-3-trifluoromethyl-pyrazol-1-yl)-acetyl]-1',2',3',4',5',6'-hexahydro-[4,4']bipyridinyl-2-carboxylic acid (R)-(1,2,3,4-tetrahydro-naphthalen-1-yl)-amide (compound A-1.6) and (B) a fungicide selected from acibenzolar-S-methyl, ametoctradin, amisulbrom, azoxystrobin, benthiavalicarb, chlorothalonil, copper, cyazofamid, cymoxanil, disodium phosphonate, dimethomorph, dithianon, famoxadone, fenamidone, fluazinam, flumorph, flupicolide, folpet, fosetyl-Al, iprovalicarb, isopyrazam, mancozeb, mandipropamid, mefenoxam, metalaxyl, pyraclostrobin, solatenol, trifloxystrobin and 3-difluoromethyl-1-methyl-1H-pyrazole-4-carboxylic acid methoxy-[1-methyl-2-(2,4,6-trichlorophenyl)-ethyl]-amide.

The present invention also relates to a composition comprising as component (A) 1'-[2-(5-cyclopropyl-3-difluoromethyl-pyrazol-1-yl)-acetyl]-1',2',3',4',5',6'-hexa-hydro-[4,4']bi-pyridinyl-2-carboxylic acid (R)-(1,2,3,4-tetrahydronaphthalen-1-yl)-amide and as component (B) a fungicide selected from ametoctradin, amisulbrom, azoxystrobin, chlorothalonil, cymoxanil, dimethomorph, dithianon, famoxadone, fenamidone, fluazinam, flupicolide, folpet, fosethyl-Al, iprovalicarb, mancozeb, mandipropamid, mefenoxam, and zoxamid.

The compositions according to the invention are effective against harmful microorganisms, such as microorganisms, that cause phytopathogenic diseases, in particular against phytopathogenic fungi and bacteria.

The compositions according to the invention are effective especially against phytopathogenic fungi belonging to the following classes: Ascomycetes (e.g. *Venturia, Podosphaera, Erysiphe, Monilinia, Mycosphaerella, Uncinula*); Basidiomycetes (e.g. the genus *Hemileia, Rhizoctonia, Phakopsora, Puccinia, Ustilago, Tilletia*); Fungi imperfecti (also known as Deuteromycetes; e.g. *Botrytis, Helminthosporium, Rhynchosporium, Fusarium, Septoria, Cercospora, Alternaria, Pyricularia* and *Pseudocercosporella*); Oomycetes (e.g. *Phytophthora, Peronospora, Pseudoperonospora, Albugo, Bremia, Pythium, Pseudosclerospora, Plasmopara*).

According to the invention "useful plants" typically comprise the following species of plants: grape vines; cereals, such as wheat, barley, rye or oats; beet, such as sugar beet or fodder beet; fruits, such as pomes, stone fruits or soft fruits, for example apples, pears, plums, peaches, almonds, cherries, strawberries, raspberries or blackberries; leguminous plants, such as beans, lentils, peas or soybeans; oil plants, such as rape, mustard, poppy, olives, sunflowers, coconut, castor oil plants, cocoa beans or groundnuts; cucumber plants, such as marrows, cucumbers or melons; fibre plants, such as cotton, flax, hemp or jute; citrus fruit, such as oranges, lemons, grapefruit or mandarins; vegetables, such as spinach, lettuce, asparagus, cabbages, carrots, onions, tomatoes, potatoes, cucurbits or paprika; lauraceae, such as avocados, cinnamon or camphor; maize; tobacco; nuts; coffee; sugar cane; tea; vines; hops; durian; bananas; natural rubber plants; turf or ornamentals, such as flowers, shrubs, broad-leaved trees or evergreens, for example conifers. This list does not represent any limitation.

The term "useful plants" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors or PPO (protoporphyrinogen-oxidase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as including also useful plants which have been so transformed by the use of recombinant DNA techniques that they are capable of synthesising one or more selectively acting toxins, such as are known, for example, from toxin-producing bacteria, especially those of the genus *Bacillus*.

The term "useful plants" is to be understood as including also useful plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

The term "locus" of a useful plant as used herein is intended to embrace the place on which the useful plants are growing, where the plant propagation materials of the useful plants are sown or where the plant propagation materials of the useful plants will be placed into the soil. An example for such a locus is a field, on which crop plants are growing.

The term "plant propagation material" is understood to denote generative parts of the plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds.

The compositions of the present invention may also be used in the field of protecting storage goods against attack of fungi. According to the present invention, the term "storage goods" is understood to denote natural substances of vegetable and/or animal origin and their processed forms, which have been taken from the natural life cycle and for which long-term protection is desired. Storage goods of vegetable origin, such as plants or parts thereof, for example stalks, leafs, tubers, seeds, fruits or grains, can be protected in the freshly harvested state or in processed form, such as pre-dried, moistened, comminuted, ground, pressed or roasted. Also falling under the definition of storage goods is timber, whether in the form of crude timber, such as construction timber, electricity pylons and barriers, or in the form of finished articles, such as furniture or objects made from wood. Storage goods of animal origin are hides, leather, furs, hairs and the like. The compositions according the present invention can prevent disadvantageous effects such as decay, discoloration or mold. Preferably "storage goods" is understood to denote natural substances of vegetable origin and/or their processed forms, more preferably fruits and their processed forms, such as pomes, stone fruits, soft fruits and citrus fruits and their processed forms. In another preferred embodiment of the invention "storage goods" is understood to denote wood. Therefore a further aspect of the present invention is a method of protecting storage goods, which comprises applying to the storage goods a composition according to the invention.

The compositions of the present invention may also be used in the field of protecting technical material against attack of fungi. According to the present invention, the term "technical material" includes paper; carpets; constructions; cooling and heating systems; wall-boards; ventilation and air conditioning systems and the like; preferably "technical material" is understood to denote wall-boards. The compositions according the present invention can prevent disadvantageous effects such as decay, discoloration or mold.

The compositions according to the invention are particularly effective against Oomycetes diseases, such as downy mildew, late blight and damping off diseases; especially against *Phytophthora* spp. in potatoes, tomatoes, cucurbits and peppers; *Plasmopora viticola* in grapes, *Pseudoperonospora cubensis* in cucurbits, *Pythium* spp. in grape.

The compositions according to the invention are furthermore particularly effective against seedborne and soilborne diseases, such as *Alternaria* spp., *Ascochyta* spp., *Botrytis cinerea*, *Cercospora* spp., *Claviceps purpurea*, *Cochliobolus sativus*, *Colletotrichum* spp., *Epicoccum* spp., *Fusarium graminearum*, *Fusarium moniliforme*, *Fusarium oxysporum*, *Fusarium proliferatum*, *Fusarium solani*, *Fusarium subglutinans*, *Gaumannomyces graminis*, *Helminthosporium* spp., *Microdochium nivale*, *Phoma* spp., *Pyrenophora graminea*, *Pyricularia oryzae*, *Rhizoctonia solani*, *Rhizoctonia cerealis*, *Sclerotinia* spp., *Septoria* spp., *Sphacelotheca reilliana*, *Tilletia* spp., *Typhula incarnata*, *Urocystis occulta*, *Ustilago* spp. or *Verticillium* spp.; in particular against pathogens of cereals, such as wheat, barley, rye or oats; maize; rice; cotton; soybean; turf; sugarbeet; oil seed rape; potatoes; pulse crops, such as peas, lentils or chickpea; and sunflower.

The compositions according to the invention are furthermore particularly effective against post harvest diseasese such as *Botrytis cinerea*, *Colletotrichum musae*, *Curvularia lunata*, *Fusarium semitecum*, *Geotrichum candidum*, *Monilinia fructicola*, *Monilinia fructigena*, *Monilinia laxa*, *Mucor piriformis*, *Penicilium italicum*, *Penicilium solitum*, *Penicillium digitatum* or *Penicillium expansum* in particular against pathogens of fruits, such as pomefruits, for example apples and pears, stone fruits, for example peaches and plums, citrus, melons, papaya, kiwi, mango, berries, for example strawberries, avocados, pomegranates and bananas, and nuts.

The compositions according to the invention are particularly useful for controlling the following diseases on the following crops. The invention therefore also encompasses a method of controlling *Alternaria* species in fruit and vegetables and potato; *Botrytis cinerea* in strawberries, tomatoes, sunflower, pulse crops, vegetables and grapes; *Plasmopara viticola* in grape; *Plasmopara halstedii* in sunflower; *Plasmopara obducens* in impatiens; *Phytophthora capsici* in cucurbits, pepper, tomato, eggplant, snap and lima beans; *Peronspora destructor* and *Phytophthora porri* in onions, *Phytophthora infestans* in potato and tomato; *Phytophthora erythroseptica* in potato; *Phytophthora melonis* in melon; *Phytophthora megasperma* in asparagus, *Phytophthora brassicae* in cabbages, *Phytophthora parasitica* in brassicas and solanaceous crops, *Peronospora vicia* in legume crops, *Bremia lactucae* in lettuce; *Pseudoperonospora cubensis* in cucumber, cucurbits, squash, luffa and melon and *Peronospora sparsa* in roses, *Albugo* spp spinach and beets, *Aphanomyces euteiches* in beets and legume crops, *Pythium* spp in potato and vegetable crops, *Rhizoctonia solani* in potato and vegetables, *Uncinula necator*, *Phomopsis viticola*, *Elsinoe ampelina*, *Pseudospezicula tracheifila*, *Glomerella cingulata*, *Guignardia bidwelli* in grape, *Cladosporium cucumerinum*, *Didymella bryoniae*, *Sphaerotheca fuliginea* and *Glomerella lagenarium* in cucurbits, *Leveillula taurica* in cucurbits and solanacious crops, *Fusarium* spp in fruits and vegetables, which comprises applying to said plants, to the locus thereof, or to propagation material thereof a composition according to claim 1.

In general, the weight ratio of component (A) to component (B) is from 2000:1 to 1:1000. The weight ratio of component (A) to component (B) is preferably from 100:1 to 1:100; more preferably from 20:1 to 1:50 and most preferably 10:1 to 1:10.

Alternatively, the weight ratio of (A) to (B) is from 100:1 to 1:1000, preferably from 10:1 to 1:200, and even more preferably from 5:1 to 1:100.

It has been found, surprisingly, that certain weight ratios of component (A) to component (B) are able to give rise to synergistic activity. Therefore, a further aspect of the invention are compositions, wherein component (A) and component (B) are present in the composition in amounts producing a synergistic effect. This synergistic activity is apparent from the fact that the fungicidal activity of the composition comprising component (A) and component (B) is greater than the sum of the fungicidal activities of component (A) and of component (B). This synergistic activity extends the range of action of component (A) and component (B) in two ways. Firstly, the rates of application of component (A) and component (B) are lowered whilst the action remains equally good, meaning that the active ingredient mixture still achieves a high degree of phytopathogen control even where the two individual components have become totally ineffective in such a low application rate range. Secondly, there is a substantial broadening of the spectrum of phytopathogens that can be controlled.

A synergistic effect exists whenever the action of an active ingredient combination is greater than the sum of the actions of the individual components. The action to be expected E for a given active ingredient combination obeys the so-called COLBY formula and can be calculated as follows (COLBY, S. R. "Calculating synergistic and antagonistic responses of herbicide combination". Weeds, Vol. 15, pages 20-22; 1967):

ppm=milligrams of active ingredient (=a.i.) per liter of spray mixture

X=% action by active ingredient A) using p ppm of active ingredient

Y=% action by active ingredient B) using q ppm of active ingredient.

According to COLBY, the expected (additive) action of active ingredients A)+B) using p+q ppm of active ingredient is $$E = X + Y - \frac{X \cdot Y}{100}$$

If the action actually observed (O) is greater than the expected action (E), then the action of the combination is super-additive, i.e. there is a synergistic effect. In mathematical terms, synergism corresponds to a positive value for the difference of (O-E). In the case of purely complementary addition of activities (expected activity), said difference (O-E) is zero. A negative value of said difference (O-E) signals a loss of activity compared to the expected activity.

However, besides the actual synergistic action with respect to fungicidal activity, the compositions according to the invention can also have further surprising advantageous properties. Examples of such advantageous properties that may be mentioned are: more advantageuos degradability; improved toxicological and/or ecotoxicological behaviour; or improved characteristics of the useful plants including: emergence, crop yields, more developed root system, tillering increase, increase in plant height, bigger leaf blade, less dead basal leaves, stronger tillers, greener leaf colour, less fertilizers needed, less seeds needed, more productive tillers, earlier flowering, early grain maturity, less plant verse (lodging), increased shoot growth, improved plant vigor, and early germination.

Some compositions according to the invention have a systemic action and can be used as foliar, soil and seed treatment fungicides.

With the compositions according to the invention it is possible to inhibit or destroy the phytopathogenic microorganisms which occur in plants or in parts of plants (fruit, blossoms, leaves, stems, tubers, roots) in different useful plants, while at the same time the parts of plants which grow later are also protected from attack by phytopathogenic microorganisms.

The compositions according to the invention can be applied to the phytopathogenic microorganisms, the useful plants, the locus thereof, the propagation material thereof, storage goods or technical materials threatened by microorganism attack.

The compositions according to the invention may be applied before or after infection of the useful plants, the propagation material thereof, storage goods or technical materials by the microorganisms.

The amount of a composition according to the invention to be applied, will depend on various factors, such as the compounds employed; the subject of the treatment, such as, for example plants, soil or seeds; the type of treatment, such as, for example spraying, dusting or seed dressing; the purpose of the treatment, such as, for example prophylactic or therapeutic; the type of fungi to be controlled or the application time.

When applied to the useful plants component (A) is typically applied at a rate of 5 to 2000 g a.i./ha, particularly 10 to 1000 g a.i./ha, e.g. 50, 75, 100 or 200 g a.i./ha, typically in association with 1 to 5000 g a.i./ha, particularly 2 to 2000 g a.i./ha, e.g. 100, 250, 500, 800, 1000, 1500 g a.i./ha of component (B).

In agricultural practice the application rates of the compositions according to the invention depend on the type of effect desired, and typically range from 20 to 4000 g of total composition per hectare.

When the compositions according to the invention are used for treating seed, rates of 0.001 to 50 g of a compound of component (A) per kg of seed, preferably from 0.01 to 10 g per kg of seed, and 0.001 to 50 g of a compound of component (B), per kg of seed, preferably from 0.01 to 10 g per kg of seed, are generally sufficient.

The composition of the invention may be employed in any conventional form, for example in the form of a twin pack, a powder for dry seed treatment (DS), an emulsion for seed treatment (ES), a flowable concentrate for seed treatment (FS), a solution for seed treatment (LS), a water dispersible powder for seed treatment (WS), a capsule suspension for seed treatment (CF), a gel for seed treatment (GF), an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP) or any technically feasible formulation in combination with agriculturally acceptable adjuvants.

Such compositions may be produced in conventional manner, e.g. by mixing the active ingredients with at least one appropriate inert formulation adjuvant (for example, diluents, solvents, fillers and optionally other formulating ingredients such as surfactants, biocides, anti-freeze, stickers, thickeners and compounds that provide adjuvancy effects). Also conventional slow release formulations may be employed where long lasting efficacy is intended. Particularly formulations to be applied in spraying forms, such as water dispersible concentrates (e.g. EC, SC, DC, OD, SE, EW, EO and the like), wettable powders and granules, may contain surfactants such as wetting and dispersing agents and other compounds that provide adjuvancy effects, e.g. the condensation product of formaldehyde with naphthalene sulphonate, an alkylarylsulphonate, a lignin sulphonate, a fatty alkyl sulphate, and ethoxylated alkylphenol and an ethoxylated fatty alcohol.

The compositions according to the invention may also comprise further pesticides, such as, for example, fungicides, insecticides or herbicides.

A seed dressing formulation is applied in a manner known per se to the seeds employing the compositions according to the invention and a diluent in suitable seed dressing formulation form, e.g. as an aqueous suspension or in a dry powder form having good adherence to the seeds. Such seed dressing formulations are known in the art. Seed dressing formulations may contain the single active ingredients or the combination of active ingredients in encapsulated form, e.g. as slow release capsules or microcapsules.

In general, the formulations include from 0.01 to 90% by weight of active agent, from 0 to 20% agriculturally acceptable surfactant and 10 to 99.99% solid or liquid formulation inerts and adjuvant(s), the active agent consisting of at least a compound of component (A) together with a compound of component (B), and optionally other active agents, particularly microbiocides or conservatives or the like. Concentrated forms of compositions generally contain in between about 2 and 80%, preferably between about 5 and 70% by weight of active agent. Application forms of formulation may for example contain from 0.01 to 20% by weight, preferably from 0.01 to 5% by weight of active agent. Whereas commercial products will preferably be formulated as concentrates, the end user will normally employ diluted formulations.

Surprisingly it has been found that compounds of formula (I)

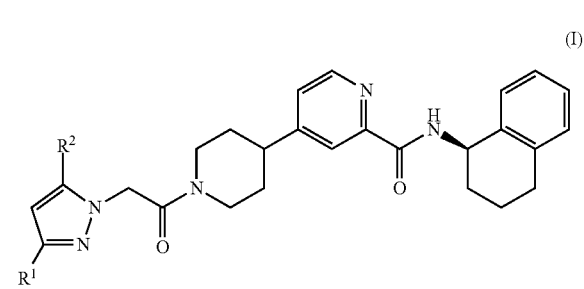

wherein $R^1$ is difluoromethyl or trifluoromethyl and $R^2$ is methyl, difluoromethyl, trifluoromethyl or cyclopropyl;

have good activity against foliar Oomycetes diseases, such as late blight and downy mildew diseases, such as *Phytophthora infestans* and *Plasmopara viticola*.

Accordingly a further aspect of the present invention is a method of controlling diseases on fruits and vegetables caused by phytopathogens, especially Oomycetes diseases, which comprises applying to the plants, the locus thereof or propagation material thereof a composition comprising a compound of formula (I).

Preferred is a method wherein the phytopathogen is *Phytophthora infestans*.

Further preferred is a method wherein the phytopathogen is *Plasmopara viticola*.

Preferred is a method, which comprises applying to the plants or to the locus thereof a composition comprising a compound of formula (I), preferably to the plants.

Further prefered is a method, which comprises applying to the propagation material of the plants a composition comprising a compound of formula (I).

The methods according to the invention, especially when a compound of formula (I) is used in combination with at least one compound (B) as described above, also allows good control of other harmful fungi frequently encountered in cereal plants. The most important fungal Oomycetes diseases in plants being *Phytophthora* spp, *Phytophtora infestans, Plasmopara viticola, Pseudoperonospora cubensis* and *Phytophthora capsicii*.

Preferred is a method of controlling diseases on fruits and vegetables, especially caused by Oomycetes diseases, which comprises applying to the useful plants, the locus thereof or propagation material thereof a composition comprising a compound of formula (I)

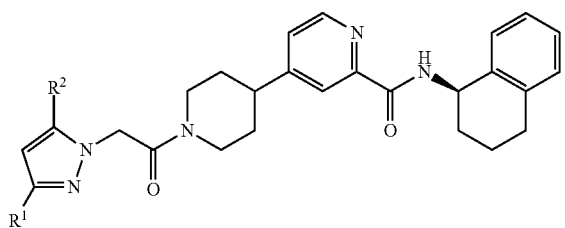

(I)

wherein $R^1$ is difluoromethyl or trifluoromethyl and $R^2$ is methyl, difluoromethyl, trifluoromethyl or cyclopropyl.

Further characteristics of compositions comprising compounds of formula (I), their application methods to cereals and their use rates are as described for compositions comprising compounds of formula (I) and additionally at least one component (B) as described above. Their application can be both before and after the infection of the plants or parts thereof with the fungi. The treatment is preferably carried out prior to the infection. When a compound of formula (I) is used on its own, the application rates in the method according to the invention are as described above, e.g. typical are rates of 5 to 2000 g a.i./ha, particularly 10 to 1000 g a.i./ha, e.g. 50, 75, 100 or 200 g a.i./ha. Compounds of formula (I) can be applied to the plants once or more than once during a growing season. For use in the method according to the invention, the compounds of formula (I) can be converted into the customary formulations described above, e.g. solutions, emulsions, suspensions, dusts, powders, pastes and granules. The use form will depend on the particular intended purpose; in each case, it should ensure a fine and even distribution of the compound of formula (I).

The term "plant" as used herein includes seedlings, bushes and crops of fruits and vegetables.

The Examples which follow serve to illustrate the invention, "active ingredient" denotes a mixture of component (A) and component (B) in a specific mixing ratio. The same formulations can be used for compositions comprising only a compound of formula (I) as the active ingredient.

Formulation Examples

| Wettable powders | a) | b) |
|---|---|---|
| active ingredient [A):B) = 1:3(a), 1:1(b)] | 25% | 75% |
| sodium lignosulfonate | 5% | — |
| sodium lauryl sulfate | 3% | 5% |
| sodium diisobutylnaphthalenesulfonate (7-8 mol of ethylene oxide) | — | 10% |
| highly dispersed silicic acid | 5% | 10% |
| kaolin | 62% | — |

The active ingredient is thoroughly mixed with the other formulation components and the mixture is thoroughly ground in a suitable mill, affording wettable powders that can be diluted with water to give suspensions of the desired concentration.

| Powders for dry seed treatment | a) | b) |
|---|---|---|
| active ingredient [A):B) = 1:3(a), 1:1(b)] | 25% | 75% |
| light mineral oil | 5% | 5% |
| highly dispersed silicic acid | 5% | — |
| kaolin | 65% | — |
| talc | — | 20 |

The active ingredient is thoroughly mixed with the other formulation components and the mixture is thoroughly ground in a suitable mill, affording powders that can be used directly for seed treatment.

| Emulsifiable concentrate | |
|---|---|
| active ingredient (A):B) = 1:6) | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| cyclohexanone | 30% |
| xylene mixture | 50% |

Emulsions of any required dilution, which can be used in plant protection, can be obtained from this concentrate by dilution with water.

| Dustable powders | a) | b) |
|---|---|---|
| active ingredient [A):B) = 1:6(a), 1:10(b)] | 5% | 6% |
| talcum | 95% | — |
| kaolin | — | 94% |

Ready-for-use dusts are obtained by mixing the active ingredient with the carriers and grinding the mixture in a suitable mill. Such powders can also be used for dry dressings for seed.

| Extruded granules | % w/w |
|---|---|
| active ingredient (A):B) = 2:1) | 15% |
| sodium lignosulfonate | 2% |
| sodium alkyl naphthalene sulfonate | 1% |
| kaolin | 82% |

The active ingredient is mixed and ground with the other formulation components, and the mixture is moistened with water. The mixture is extruded and then dried in a stream of air.

| Suspension concentrate | |
|---|---|
| active ingredient (A):B) = 1:8 | 40% |
| propylene glycol | 10% |
| nonylphenol polyethylene glycol ether (15 mol of ethylene oxide) | 6% |
| sodium lignosulfonate | 10% |
| carboxymethylcellulose | 1% |
| silicone oil (in the form of a 75% emulsion in water) | 1% |
| water | 32% |

The finely ground active ingredient is intimately mixed with the other formulation components, giving a suspension concentrate which can be diluted in water at any desired rate. Using such dilutions, living plants as well as plant propagation material can be treated and protected against infestation by microorganisms, by spraying, pouring or immersion.

| Flowable concentrate for seed treatment | |
|---|---|
| active ingredient (A):B) = 1:8 | 40% |
| propylene glycol | 5% |
| copolymer butanol PO/EO | 2% |
| tristyrenephenole ethoxylate (with 10-20 moles EO) | 2% |
| 1,2-benzisothiazolin-3-one | 0.5% |
| monoazo-pigment calcium salt | 5% |
| silicone oil (in the form of a 75% emulsion in water) | 0.2% |
| water | 45.3% |

The finely ground active ingredient is intimately mixed with the other formulation components, giving a suspension concentrate which can be diluted further in water to be applied to seeds. Using such dilutions, propagation material can be treated and protected against infestation by microorganisms, by spraying, pouring or immersion.

Biological Examples

In the following examples, the expected fungicidal action is calculated according to the Colby method disclosed above. The results are given in Tables B1, B2 and B3:

Example B1: Preventive Action Against Phytophthora Infestans on Tomato

Tomato plants cultivar Roter Gnom are grown in the greenhouse for 2 weeks. 2 days after spraying the fungicide, plants are inoculated with a spore suspension of Phytophthora infestans. Plants were evaluated 4 days after inoculation for % infected leaf area. Per treatment, 4 pots with 1 plants each were assessed. Results are given in % disease control:

[(% disease control] treatment=(1-([% infected area] treatment/[% infected area] control))*100.

TABLE B1.1

| Compound A-1.2 rate (ppm) | Mandipropamid rate (ppm) | % disease control | expected action (Colby) |
|---|---|---|---|
| 0.06 | | 14 | |
| 0.02 | | 0 | |
| | 0.6 | 3 | |
| | 0.2 | 0 | |
| | 0.06 | 0 | |
| 0.06 | 0.6 | 64 | 16.6 |
| 0.06 | 0.2 | 47 | 14 |
| 0.06 | 0.06 | 39 | 14 |
| 0.02 | 0.6 | 65 | 3 |

TABLE B1.1-continued

| Compound A-1.2 rate (ppm) | Mandipropamid rate (ppm) | % disease control | expected action (Colby) |
|---|---|---|---|
| 0.02 | 0.2 | 53 | 0 |
| 0.02 | 0.06 | 58 | 0 |

TABLE B1.2

| Compound A-1.2 rate (ppm) | Folpet rate (ppm) | % disease control | expected action (Colby) |
|---|---|---|---|
| 0.06 | | 14 | |
| | 60 | 33 | |
| | 20 | 0 | |
| 0.06 | 60 | 61 | 42.2 |
| 0.06 | 20 | 58 | 14 |

TABLE B1.3

| Compound A-1.2 rate (ppm) | Chlorothalonil rate (ppm) | % disease control | expected action (Colby) |
|---|---|---|---|
| 0.06 | | 14 | |
| | 60 | 6 | |
| 0.06 | 60 | 72 | 19.2 |

Example B2: Field Activity Against Plasmopara Viticola on Grapevine

Merlot grapevines were cultivated in rows with 1 m between plants within the row, and 2 m spaces between rows. Treatment plots were defined with an 8 m² vertical area. The trial consisted of three replicates of the treatment list, with the positions of each treatment plot randomised within the replicate.

Test compounds were formulated and applied to the relevant treatment plots, using a backpack sprayer with a flat fan nozzle. The first application was made when the majority of plants were at growth stage BBCH 15 and following applications at 10-14 day intervals through to growth stage BBCH 79.

The first symptoms of the target pathogen Plasmopara viticola were observed between the second and third applications. Plants outside the trial area were inoculated to increase the disease pressure, but infection processes within the trial plots were natural. Fungicide products known to have no effect on Plasmopara were used to maintain the trial against non-target pathogens, alongside a standard insecticide and herbicide treatment program to control other pests.

Ten days after the sixth application, at growth stage BBCH 79, the fruit was assessed for infection by Plasmopara viticola. 50 bunches per plot were assessed, the scores given in table B2 are percent disease control relative to untreated, based on the mean percentage of bunches showing symptoms of infection across all three replicates of a treatment.

TABLE B2

| Compound A-1.2 Rate (gai/ha) | Mandipropamid Rate (gai/ha) | % disease control relative to untreated[1] | Expected activity (Colby) |
|---|---|---|---|
| 22.5 | | 87.3 | |
| | 93.75 | 17.3 | |
| 22.5 | 93.75 | 100.0 | 89.5 |

[1] untreated plots had a 100% incidence of infection on the assessed bunches

Example B3: Field Activity Against *Phytophthora Infestans* on Potato

Potato plants (variety Bintje) were cultivated in the field, and 5 m² treatment plots marked out. Test compounds were formulated and applied using a boom sprayer, with the first application when the majority of plants were at growth stage BBCH 16, and three further applications at 14-15 day intervals until growth stage BBCH 67. The trial consisted of three replicate blocks, with the position of the treatment plots randomised within each block.

The test plots were inoculated with *Phytophthora infestans* one day after the first application. Buffer strips between plots and between the replicate blocks also provided a source of secondary infection of the treatment plots over the course of the trial.

Four days after the final application the treated plots were assessed for the severity of infection by *Phytophthora infestans*. Two subsamples were taken in each replicate plot, and the percentage of leaf area affected by *Phytophthora infestans* lesions was assessed. Table B3 gives the mean percent control relative to untreated accross the three replicates of each treatment.

TABLE B3

| Compound A-1.2 Rate (gai/ha) | Chlorothalonil Rate (gai/ha) | % disease control relative to untreated[1] | Expected activity (Colby) |
|---|---|---|---|
| 15 |  | 64.8 |  |
|  | 1000 | 4.3 |  |
| 15 | 1000 | 84.6 | 66.3 |

[1]untreated plots had mean score of 99.3% lesion coverage on the assessed plants Examples B4 to B21: Activity Against *Phytophthora Capsici*

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is determined photometrically 3-4 days after application. Table B4 to B21 gives the mean percent control relative to untreated.

TABLE B4

| Compound A-1.2 (ppm) | Mancozeb (ppm) | % disease control | Expected action (Colby) |
|---|---|---|---|
| 0.0000625 |  | 0 |  |
| 0.0001250 |  | 32 |  |
| 0.0002500 |  | 64 |  |
| 0.0005000 |  | 76 |  |
|  | 0.3125 | 3 |  |
|  | 0.6250 | 1 |  |
|  | 1.2500 | 0 |  |
|  | 2.5000 | 0 |  |
|  | 5.0000 | 1 |  |
|  | 10.0000 | 1 |  |
|  | 20.0000 | 0 |  |
| 0.0000625 | 0.3125 | 52 | 3 |
| 0.0000625 | 0.6250 | 34 | 1 |
| 0.0001250 | 0.6250 | 57 | 32 |
| 0.0001250 | 1.2500 | 81 | 32 |
| 0.0001250 | 2.5000 | 72 | 32 |
| 0.0001250 | 5.0000 | 72 | 33 |
| 0.0001250 | 10.0000 | 68 | 33 |
| 0.0002500 | 1.2500 | 89 | 64 |

TABLE B4-continued

| Compound A-1.2 (ppm) | Mancozeb (ppm) | % disease control | Expected action (Colby) |
|---|---|---|---|
| 0.0002500 | 2.5000 | 82 | 64 |
| 0.0002500 | 5.0000 | 87 | 65 |
| 0.0002500 | 10.0000 | 75 | 65 |
| 0.0002500 | 20.0000 | 86 | 64 |
| 0.0005000 | 2.5000 | 94 | 76 |
| 0.0005000 | 5.0000 | 90 | 76 |
| 0.0005000 | 10.0000 | 87 | 76 |
| 0.0005000 | 20.0000 | 88 | 76 |

TABLE B5

| Compound A-1.2 (ppm) | Chlorothalonil (ppm) | % disease control | Expected action (Colby) |
|---|---|---|---|
| 0.0000020 |  | 0 |  |
| 0.0000039 |  | 0 |  |
| 0.0000078 |  | 0 |  |
| 0.0000156 |  | 0 |  |
| 0.0000313 |  | 0 |  |
| 0.0000625 |  | 47 |  |
|  | 0.0781 | 24 |  |
|  | 0.1563 | 24 |  |
|  | 0.3125 | 23 |  |
|  | 0.6250 | 64 |  |
| 0.0000020 | 0.0781 | 62 | 24 |
| 0.0000020 | 0.1563 | 56 | 24 |
| 0.0000039 | 0.0781 | 45 | 24 |
| 0.0000039 | 0.1563 | 63 | 24 |
| 0.0000039 | 0.3125 | 76 | 23 |
| 0.0000078 | 0.1563 | 47 | 24 |
| 0.0000078 | 0.3125 | 64 | 23 |
| 0.0000078 | 0.6250 | 89 | 64 |
| 0.0000156 | 0.0781 | 50 | 24 |
| 0.0000156 | 0.1563 | 37 | 24 |
| 0.0000156 | 0.3125 | 64 | 23 |
| 0.0000156 | 0.6250 | 87 | 64 |
| 0.0000313 | 0.1563 | 50 | 24 |
| 0.0000313 | 0.3125 | 37 | 23 |
| 0.0000313 | 0.6250 | 87 | 64 |
| 0.0000625 | 0.3125 | 88 | 59 |

TABLE B6

| Compound A-1.2 (ppm) | Dithianon (ppm) | % disease control | Expected action (Colby) |
|---|---|---|---|
| 0.0000625 |  | 0 |  |
| 0.0001250 |  | 40 |  |
| 0.0002500 |  | 78 |  |
|  | 0.1250 | 0 |  |
|  | 0.2500 | 7 |  |
|  | 0.5000 | 8 |  |
|  | 1.0000 | 25 |  |
| 0.0000625 | 0.5000 | 47 | 8 |
| 0.0001250 | 0.1250 | 56 | 40 |
| 0.0001250 | 0.2500 | 68 | 44 |
| 0.0001250 | 0.5000 | 74 | 45 |
| 0.0001250 | 1.0000 | 80 | 55 |
| 0.0002500 | 0.1250 | 87 | 78 |

TABLE B7

| Compound A-1.2 (ppm) | Azoxystrobin (ppm) | % disease control | Expected action (Colby) |
|---|---|---|---|
| 0.0000039 |  | 0 |  |
| 0.0000078 |  | 0 |  |
| 0.0000156 |  | 0 |  |
| 0.0000313 |  | 0 |  |
| 0.0000625 |  | 38 |  |

TABLE B7-continued

| Compound A-1.2 (ppm) | Azoxystrobin (ppm) | % disease control | Expected action (Colby) |
|---|---|---|---|
| 0.0001250 | | 42 | |
| | 0.0313 | 23 | |
| | 0.0625 | 23 | |
| | 0.1250 | 62 | |
| 0.0000039 | 0.0313 | 50 | 23 |
| 0.0000078 | 0.0313 | 50 | 23 |
| 0.0000078 | 0.0625 | 54 | 23 |
| 0.0000156 | 0.0625 | 51 | 23 |
| 0.0000156 | 0.1250 | 61 | 62 |
| 0.0000313 | 0.0625 | 54 | 23 |
| 0.0000313 | 0.1250 | 79 | 62 |
| 0.0000625 | 0.0313 | 62 | 52 |
| 0.0000625 | 0.0625 | 61 | 52 |
| 0.0001250 | 0.0625 | 88 | 55 |

TABLE B8

| Compound A-1.2 (ppm) | Mefenoxam (ppm) | % disease control | Expected action (Colby) |
|---|---|---|---|
| 0.0000625 | | 3 | |
| 0.0001250 | | 56 | |
| 0.0002500 | | 69 | |
| | 0.0031 | 0 | |
| | 0.0063 | 13 | |
| | 0.0125 | 13 | |
| | 0.0250 | 28 | |
| | 0.0500 | 42 | |
| 0.0000625 | 0.0031 | 36 | 3 |
| 0.0000625 | 0.0125 | 34 | 16 |
| 0.0000625 | 0.0250 | 44 | 31 |
| 0.0000625 | 0.0500 | 57 | 44 |
| 0.0001250 | 0.0063 | 71 | 62 |
| 0.0001250 | 0.0125 | 68 | 62 |
| 0.0002500 | 0.0125 | 87 | 73 |

TABLE B9

| Compound A-1.2 (ppm) | Mandipropamid (ppm) | % disease control | Expected action (Colby) |
|---|---|---|---|
| 0.0000625 | | 0 | |
| 0.0001250 | | 47 | |
| | 0.0003 | 16 | |
| | 0.0006 | 0 | |
| | 0.0012 | 0 | |
| | 0.0025 | 17 | |
| | 0.0050 | 13 | |
| | 0.0100 | 15 | |
| 0.0000625 | 0.0003 | 36 | 16 |
| 0.0000625 | 0.0050 | 34 | 13 |
| 0.0001250 | 0.0006 | 74 | 47 |
| 0.0001250 | 0.0012 | 71 | 47 |
| 0.0001250 | 0.0025 | 80 | 56 |
| 0.0001250 | 0.0100 | 89 | 55 |

TABLE B10

| Compound A-1.2 (ppm) | Dimetomorph (ppm) | % disease control | Expected action (Colby) |
|---|---|---|---|
| 0.0000625 | | 12 | |
| 0.0001250 | | 62 | |
| | 0.0031 | 0 | |
| | 0.0063 | 14 | |
| | 0.0125 | 0 | |
| | 0.1000 | 28 | |
| 0.0000625 | 0.0031 | 51 | 12 |
| 0.0000625 | 0.0063 | 35 | 24 |
| 0.0001250 | 0.0063 | 81 | 67 |

TABLE B10-continued

| Compound A-1.2 (ppm) | Dimetomorph (ppm) | % disease control | Expected action (Colby) |
|---|---|---|---|
| 0.0001250 | 0.0125 | 80 | 62 |
| 0.0001250 | 0.1000 | 91 | 72 |

TABLE B11

| Compound A-1.2 (ppm) | Fluazinam (ppm) | % disease control | Expected action (Colby) |
|---|---|---|---|
| 0.0000625 | | 0 | |
| 0.0001250 | | 55 | |
| 0.0002500 | | 82 | |
| | 0.0625 | 4 | |
| | 0.1250 | 10 | |
| | 0.2500 | 0 | |
| | 0.5000 | 14 | |
| 0.0000625 | 0.5000 | 75 | 14 |
| 0.0001250 | 0.0625 | 75 | 57 |
| 0.0001250 | 0.1250 | 84 | 60 |
| 0.0001250 | 0.2500 | 72 | 55 |
| 0.0001250 | 0.5000 | 74 | 62 |
| 0.0002500 | 0.1250 | 94 | 84 |
| 0.0002500 | 0.2500 | 94 | 82 |

TABLE B12

| Compound A-1.2 (ppm) | Folpet (ppm) | % disease control | Expected action (Colby) |
|---|---|---|---|
| 0.0000313 | | 0 | |
| 0.0000625 | | 0 | |
| 0.0001250 | | 57 | |
| 0.0002500 | | 81 | |
| | 0.0313 | 17 | |
| | 0.0625 | 11 | |
| | 0.1250 | 19 | |
| | 0.2500 | 19 | |
| 0.0000313 | 0.0313 | 37 | 17 |
| 0.0000313 | 0.2500 | 75 | 19 |
| 0.0000625 | 0.0625 | 38 | 11 |
| 0.0001250 | 0.1250 | 76 | 65 |
| 0.0002500 | 0.1250 | 97 | 84 |

TABLE B13

| Compound A-1.2 (ppm) | Cymoxanil (ppm) | % disease control | Expected action (Colby) |
|---|---|---|---|
| 0.0001250 | | 46 | |
| 0.0002500 | | 69 | |
| 0.0005000 | | 84 | |
| | 0.0625 | 0 | |
| | 0.1250 | 10 | |
| | 0.2500 | 0 | |
| | 0.5000 | 11 | |
| | 1.0000 | 8 | |
| | 2.0000 | 36 | |
| 0.0001250 | 0.0625 | 67 | 46 |
| 0.0001250 | 0.1250 | 64 | 51 |
| 0.0001250 | 0.2500 | 56 | 46 |
| 0.0001250 | 0.5000 | 61 | 52 |
| 0.0001250 | 1.0000 | 85 | 50 |
| 0.0002500 | 0.1250 | 90 | 72 |
| 0.0002500 | 0.2500 | 93 | 69 |
| 0.0002500 | 0.5000 | 91 | 73 |
| 0.0002500 | 1.0000 | 91 | 72 |
| 0.0002500 | 2.0000 | 91 | 80 |
| 0.0005000 | 0.2500 | 96 | 84 |
| 0.0005000 | 1.0000 | 98 | 85 |

TABLE B14

| Compound A-1.2 (ppm) | Zoxamid (ppm) | % disease control | Expected action (Colby) |
|---|---|---|---|
| 0.0000156 | | 0 | |
| 0.0000313 | | 0 | |
| 0.0000625 | | 0 | |
| | 0.0063 | 19 | |
| | 0.0125 | 40 | |
| | 0.0250 | 48 | |
| | 0.0500 | 65 | |
| 0.0000156 | 0.0125 | 49 | 40 |
| 0.0000313 | 0.0063 | 42 | 19 |
| 0.0000313 | 0.0125 | 49 | 40 |
| 0.0000313 | 0.0250 | 66 | 48 |
| 0.0000625 | 0.0063 | 55 | 19 |
| 0.0000625 | 0.0250 | 63 | 48 |
| 0.0000625 | 0.0500 | 86 | 65 |

TABLE B15

| Compound A-1.2 (ppm) | Fluopicolid (ppm) | % disease control | Expected action (Colby) |
|---|---|---|---|
| 0.0000156 | | 0 | |
| 0.0000313 | | 0 | |
| 0.0000625 | | 0 | |
| 0.0001250 | | 71 | |
| | 0.0625 | 6 | |
| | 0.1250 | 59 | |
| | 0.2500 | 69 | |
| | 0.5000 | 79 | |
| 0.0000156 | 0.1250 | 90 | 59 |
| 0.0000313 | 0.2500 | 97 | 69 |
| 0.0000625 | 0.0625 | 52 | 6 |
| 0.0000625 | 0.2500 | 97 | 69 |
| 0.0000625 | 0.5000 | 100 | 79 |
| 0.0001250 | 0.0625 | 80 | 73 |

TABLE B16

| Compound A-1.2 (ppm) | Amisulbrom (ppm) | % disease control | Expected action (Colby) |
|---|---|---|---|
| 0.0001250 | | 54 | |
| | 0.0063 | 5 | |
| | 0.0125 | 6 | |
| | 0.0500 | 24 | |
| | 0.1000 | 35 | |
| 0.0001250 | 0.0063 | 85 | 56 |
| 0.0001250 | 0.0125 | 81 | 57 |
| 0.0001250 | 0.0500 | 89 | 65 |
| 0.0001250 | 0.1000 | 89 | 70 |

TABLE B17

| Compound A-1.2 (ppm) | Ametoctradin (ppm) | % disease control | Expected action (Colby) |
|---|---|---|---|
| 0.0000625 | | 0 | |
| 0.0001250 | | 67 | |
| 0.0002500 | | 79 | |
| 0.0005000 | | 82 | |
| | 0.0063 | 8 | |
| | 0.0125 | 8 | |
| | 0.0250 | 13 | |
| | 0.0500 | 30 | |
| 0.0000625 | 0.0500 | 51 | 30 |
| 0.0001250 | 0.0063 | 81 | 70 |
| 0.0001250 | 0.0125 | 86 | 70 |
| 0.0002500 | 0.0125 | 94 | 81 |
| 0.0005000 | 0.0250 | 96 | 84 |

TABLE B18

| Compound A-1.2 (ppm) | Fenamidone (ppm) | % disease control | Expected action (Colby) |
|---|---|---|---|
| 0.0000078 | | 0 | |
| 0.0000156 | | 0 | |
| 0.0000313 | | 0 | |
| 0.0000625 | | 0 | |
| 0.0001250 | | 46 | |
| | 0.0031 | 12 | |
| | 0.0063 | 4 | |
| | 0.0125 | 41 | |
| | 0.0250 | 54 | |
| 0.0000078 | 0.0063 | 40 | 4 |
| 0.0000156 | 0.0063 | 40 | 4 |
| 0.0000156 | 0.0125 | 54 | 41 |
| 0.0000313 | 0.0125 | 55 | 41 |
| 0.0000313 | 0.0250 | 72 | 54 |
| 0.0000625 | 0.0031 | 43 | 12 |
| 0.0000625 | 0.0250 | 62 | 54 |
| 0.0001250 | 0.0063 | 61 | 48 |
| 0.0001250 | 0.0125 | 83 | 69 |

TABLE B19

| Compound A-1.2 (ppm) | Famoxadone (ppm) | % disease control | Expected action (Colby) |
|---|---|---|---|
| 0.0000156 | | 0 | |
| 0.0000313 | | 0 | |
| 0.0000625 | | 0 | |
| 0.0001250 | | 38 | |
| 0.0002500 | | 81 | |
| | 0.1563 | 16 | |
| | 0.3125 | 16 | |
| | 0.6250 | 16 | |
| | 1.2500 | 16 | |
| | 2.5000 | 16 | |
| | 5.0000 | 25 | |
| 0.0000156 | 0.1563 | 42 | 16 |
| 0.0000156 | 0.6250 | 40 | 16 |
| 0.0000313 | 0.3125 | 52 | 16 |
| 0.0000313 | 0.6250 | 44 | 16 |
| 0.0000313 | 1.2500 | 75 | 16 |
| 0.0000625 | 0.3125 | 74 | 16 |
| 0.0000625 | 0.6250 | 75 | 16 |
| 0.0000625 | 1.2500 | 51 | 16 |
| 0.0000625 | 2.5000 | 75 | 16 |
| 0.0001250 | 0.6250 | 93 | 48 |
| 0.0001250 | 1.2500 | 82 | 48 |
| 0.0001250 | 2.5000 | 75 | 48 |
| 0.0001250 | 5.0000 | 75 | 54 |
| 0.0002500 | 1.2500 | 97 | 84 |
| 0.0002500 | 2.5000 | 94 | 84 |

TABLE B20

| Compound A-1.2 (ppm) | Iprovalicarb (ppm) | % disease control | Expected action (Colby) |
|---|---|---|---|
| 0.0000625 | | 66 | |
| 0.0001250 | | 83 | |
| 0.0002500 | | 0 | |
| | 0.6250 | 0 | |
| | 1.2500 | 18 | |
| | 2.5000 | 0 | |
| | 0.6250 | 91 | 66 |
| 0.0000625 | 1.2500 | 85 | 72 |
| 0.0000625 | 2.5000 | 92 | 83 |

TABLE B21

| Compound A-1.2 (ppm) | Fosethyl-Al (ppm) | % disease control | Expected action (Colby) |
|---|---|---|---|
| 0.000063 | | 0 | |
| 0.000125 | | 69 | |
| 0.000250 | | 78 | |
| | 0.3125 | 8 | |
| | 0.6250 | 14 | |
| | 1.2500 | 14 | |
| 0.000063 | 0.3125 | 70 | 8 |
| 0.000063 | 0.6250 | 46 | 14 |
| 0.000063 | 1.2500 | 42 | 14 |
| 0.000125 | 0.6250 | 83 | 73 |
| 0.000250 | 1.2500 | 92 | 81 |

What is claimed is:

1. A composition suitable for control of diseases caused by phytopathogens comprising (A) a compound of formula I

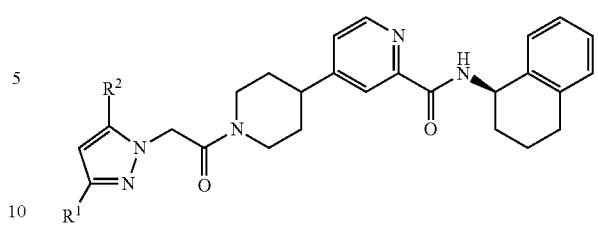

wherein $R^1$ is difluoromethyl and $R^2$ is difluoromethyl; and (B) at least one compound selected from the group consisting of azoxystrobin, mefenoxam (metalaxyl-M), dimethomorph, iprovalicarb, mandipropamid, ametoctradin, amisulbrom, chlorothalonil, cymoxanil, dithianon, famoxadone, fenamidone, fluazinam, flupicolide, folpet, fosetyl-Al, mancozeb and zoxamid.

2. A composition according to claim 1, wherein the weight ratio of (A) to (B) is from 100:1 to 1:1000.

3. A composition according to claim 1, wherein the weight ratio of (A) to (B) is from 10:1 to 1:200.

4. A composition according to claim 1, wherein the weight ratio of (A) to (B) is from 5:1 to 1:100.

* * * * *